US012129276B2

(12) United States Patent
Harrison et al.

(10) Patent No.: US 12,129,276 B2
(45) Date of Patent: *Oct. 29, 2024

(54) OXYSTEROLS AND METHODS OF USE THEREOF

(71) Applicant: SAGE THERAPEUTICS, INC., Cambridge, MA (US)

(72) Inventors: Boyd L. Harrison, Princeton Junction, NJ (US); Gabriel Martinez Botella, Wayland, MA (US); Albert Jean Robichaud, Boston, MA (US); Francesco G. Salituro, Marlborough, MA (US)

(73) Assignee: SAGE THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/116,557

(22) Filed: Mar. 2, 2023

(65) Prior Publication Data

US 2023/0348526 A1 Nov. 2, 2023

Related U.S. Application Data

(63) Continuation of application No. 16/902,730, filed on Jun. 16, 2020, now abandoned, which is a continuation of application No. 16/028,790, filed on Jul. 6, 2018, now Pat. No. 10,723,758, which is a continuation of application No. 15/319,504, filed as application No. PCT/US2015/036510 on Jun. 18, 2015, now Pat. No. 10,259,840.

(60) Provisional application No. 62/107,236, filed on Jan. 23, 2015, provisional application No. 62/014,014, filed on Jun. 18, 2014.

(51) Int. Cl.

| | |
|---|---|
| *C07J 9/00* | (2006.01) |
| *A61K 9/00* | (2006.01) |
| *A61K 9/20* | (2006.01) |
| *A61K 9/48* | (2006.01) |
| *A61K 31/575* | (2006.01) |
| *C07J 13/00* | (2006.01) |
| *C07J 31/00* | (2006.01) |

(52) U.S. Cl.
CPC .............. *C07J 9/00* (2013.01); *A61K 9/0019* (2013.01); *A61K 9/0095* (2013.01); *A61K 9/2063* (2013.01); *A61K 9/4866* (2013.01); *A61K 31/575* (2013.01); *C07J 9/005* (2013.01); *C07J 13/005* (2013.01); *C07J 13/007* (2013.01); *C07J 31/006* (2013.01)

(58) Field of Classification Search
CPC ....................................................... C07J 9/00
See application file for complete search history.

(56) References Cited

U.S. PATENT DOCUMENTS

| | | | |
|---|---|---|---|
| 2,259,698 A | 10/1941 | Johannessohn et al. | |
| 2,594,323 A | 4/1952 | Levin et al. | |
| 3,079,385 A | 2/1963 | Bertin et al. | |
| 3,206,459 A | 9/1965 | Cross | |
| 4,071,625 A | 1/1978 | Grunwell et al. | |
| 5,232,917 A | 8/1993 | Bolger et al. | |
| 5,376,645 A | 12/1994 | Stella et al. | |
| 5,512,570 A | 4/1996 | Dorn et al. | |

(Continued)

FOREIGN PATENT DOCUMENTS

| | | |
|---|---|---|
| AU | 728843 | 1/2001 |
| JP | 50140435 | 11/1975 |

(Continued)

OTHER PUBLICATIONS

Berardelli et al., "EFNS/MDS-ES/ENS [corrected] recommendations for the diagnosis of Parkinson's disease," European Journal of Neurology, 20(1):16-34 (2013).
Berge et al., "Pharmaceutical salts," Journal of Pharmaceutical Sciences, 66(1):1-19 (1977).
Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).
Bukelis et al., "Smith-Lemli-Opitz syndrome and autism spectrum disorder," American Journal of Psychiatry, 164(11):1655-1661 (2007).
Cais et al., "Temperature dependence of NR1/NR2B NMDA receptor channels," Neuroscience, 151(2):428-438 (2008).
Cancer [online], [retrieved on Jul. 6, 2007]. Retrieved from the internet, URL http://www.nlm.nih.gov/medlineplus/ cancer.html> (11 pages).

(Continued)

*Primary Examiner* — Kamal A Saeed
*Assistant Examiner* — Karen Cheng
(74) *Attorney, Agent, or Firm* — HALEY GUILIANO LLP; Karen Mangasarian; Mihaela D. Danca

(57) ABSTRACT

Compounds are provided according to Formula (I) and pharmaceutically acceptable salts thereof, and pharmaceutical compositions thereof, wherein X, Y, $R^1$, $R^{2a}$, $R^{2b}$, $R^{4a}$, $R^{4b}$, $R^{5a}$, $R^{5b}$, $R^{6a}$, $R^{6b}$, $R^7$, and $R^8$ are as defined herein. Compounds of the present invention are contemplated useful for the prevention and treatment of a variety of conditions.

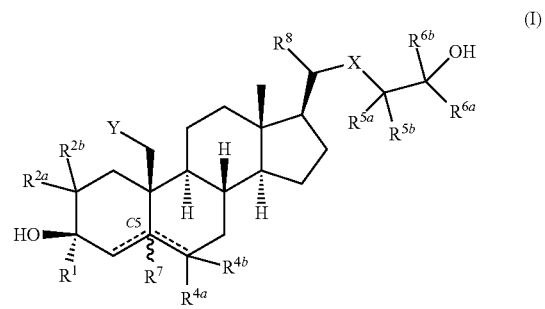

20 Claims, No Drawings

(56) References Cited

U.S. PATENT DOCUMENTS

| | | | |
|---|---|---|---|
| 5,595,996 A | 1/1997 | Graham et al. | |
| 5,888,996 A | 3/1999 | Farb | |
| 5,925,630 A | 7/1999 | Upasani et al. | |
| 6,407,086 B2 | 6/2002 | Faarup et al. | |
| 6,645,953 B2 | 11/2003 | Gronvald et al. | |
| 6,884,796 B2 | 4/2005 | Faarup et al. | |
| 6,933,312 B2 | 8/2005 | Price et al. | |
| 8,034,798 B2 | 10/2011 | Baulieu et al. | |
| 8,247,436 B2 | 8/2012 | Baettig et al. | |
| 8,604,011 B2 | 12/2013 | Mellon | |
| 8,673,843 B2 | 3/2014 | Moskal et al. | |
| 8,829,213 B2 | 9/2014 | Peng et al. | |
| 10,227,375 B2 | 3/2019 | Botella et al. | |
| 10,259,840 B2 | 4/2019 | Harrison et al. | |
| 10,696,712 B2 | 6/2020 | Salituro et al. | |
| 10,759,828 B2 | 9/2020 | Upasani et al. | |
| 11,104,701 B2 | 8/2021 | Botella et al. | |
| 11,149,056 B2 | 10/2021 | Salituro et al. | |
| 11,279,730 B2 | 3/2022 | Salituro et al. | |
| 11,407,782 B2 | 8/2022 | Martinez Botella et al. | |
| 11,613,556 B2 | 3/2023 | Salituro et al. | |
| 11,732,000 B2 | 8/2023 | Salituro et al. | |
| 11,851,457 B2 | 12/2023 | Salituro et al. | |
| 11,878,995 B2 | 1/2024 | Martinez Botella et al. | |
| 11,884,697 B2 | 1/2024 | Robichaud et al. | |
| 11,905,309 B2 | 2/2024 | Martinez Botella et al. | |
| 11,926,646 B2 | 3/2024 | Salituro et al. | |
| 2011/0112077 A1 | 5/2011 | Kuduk et al. | |
| 2011/0160223 A1 | 6/2011 | Dingledine et al. | |
| 2011/0190249 A1 | 8/2011 | Rees et al. | |
| 2012/0035156 A1 | 2/2012 | Alberati et al. | |
| 2012/0040916 A1 | 2/2012 | Moon et al. | |
| 2012/0041016 A1 | 2/2012 | Frincke | |
| 2012/0115169 A1 | 5/2012 | Mullenix et al. | |
| 2013/0210792 A1 | 8/2013 | Song et al. | |
| 2014/0045943 A1 | 2/2014 | Khan et al. | |
| 2014/0148412 A1 | 5/2014 | Hogenkamp | |
| 2014/0235600 A1 | 8/2014 | Covey et al. | |
| 2014/0335050 A1 | 11/2014 | Haggerty et al. | |
| 2015/0158903 A1 | 6/2015 | Upasani et al. | |
| 2015/0291654 A1 | 10/2015 | Upasani et al. | |
| 2015/0376225 A1 | 12/2015 | Dugar et al. | |
| 2016/0022701 A1 | 1/2016 | Reddy et al. | |
| 2016/0031930 A1 | 2/2016 | Botella et al. | |
| 2017/0305960 A1 | 10/2017 | Botella et al. | |
| 2018/0237470 A1 | 8/2018 | Botella et al. | |
| 2018/0362573 A1 | 12/2018 | Upasani et al. | |
| 2019/0127414 A1 | 5/2019 | Botella et al. | |
| 2019/0135854 A1 | 5/2019 | Harrison et al. | |
| 2021/0147470 A1 | 5/2021 | Upasani et al. | |
| 2023/0192756 A1 | 6/2023 | Upasani et al. | |

FOREIGN PATENT DOCUMENTS

| | | |
|---|---|---|
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2009545535 | 12/2009 |
| JP | 2016514967 | 5/2016 |
| RU | 2194712 C2 | 12/2002 |
| RU | 2458065 C2 | 8/2012 |
| RU | 2665571 | 8/2018 |
| WO | WO1980002562 | 11/1980 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996016076 | 5/1996 |
| WO | WO1996040043 | 12/1996 |
| WO | WO1996040151 | 12/1996 |
| WO | WO1997000884 | 1/1997 |
| WO | WO1997003677 | 2/1997 |
| WO | WO1997042215 | 11/1997 |
| WO | WO1998005337 | 2/1998 |
| WO | WO1998007740 | 2/1998 |
| WO | WO1999058497 | 11/1999 |
| WO | WO2000063228 | 10/2000 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2002090375 | 11/2002 |
| WO | WO2003039480 | 5/2003 |
| WO | WO2003049685 | 6/2003 |
| WO | WO2003082893 | 10/2003 |
| WO | WO2004055201 | 7/2004 |
| WO | WO2005079810 | 9/2005 |
| WO | WO2008041003 | 4/2008 |
| WO | WO2008063128 | 5/2008 |
| WO | WO2009001097 | 12/2008 |
| WO | WO2009059961 | 5/2009 |
| WO | WO2009073186 | 6/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2011092127 | 8/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013054822 | 4/2013 |
| WO | WO2013056181 | 4/2013 |
| WO | WO2013163455 | 10/2013 |
| WO | WO2014025942 | 2/2014 |
| WO | WO2014115167 | 7/2014 |
| WO | WO2014120786 | 8/2014 |
| WO | WO2014160441 | 10/2014 |
| WO | WO2014160480 | 10/2014 |

OTHER PUBLICATIONS

Chen et al., "The chemical biology of clinically tolerated NMDA receptor antagonists," Journal of Neurochemistry, 97(6):1611-1626 (2006).

Citraro et al., "Effects of some neurosteroids injected into some brain areas of WAG/Rij rats, an animal model of generalized absence epilepsy," Neuropharmacology, 50(8):1059-1071 (2006).

Collingridge et al., "The NMDA receptor as a target for cognitive enhancement," Neuropharmacology, 64:13-26 (2013).

Connick et al., "Program No. 613 1/B86," 2009 Neuroscience Meeting Planner, Chicago, IL: Society for Neuroscience (2009) (2 pages).

Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).

Corman et al., "Structure-activity relationships for side chain oxysterol agonists of the hedgehog signaling pathway," ACS Medicinal Chemistry Letters, 3(10):828-833 (2012).

Costa et al., "A novel family of negative and positive allosteric modulators of NMDA receptors," Journal of Pharmacology and Experimental Therapeutics, 335(3):614-621 (2010).

Cross et al., "Steroids CCLXXIN[1]. Biologically-active labile ethers IV[2]. The synthesis of 22-oxa-25-azacholesterol and related compounds," Steroids, 5(5):585-598 (1965).

Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).

(56) References Cited

OTHER PUBLICATIONS

Dayal et al., "Stereospecific synthesis of 3 beta-hydroxylated bile alcohols," Journal of Lipid Research, 25(6):646-650 (1984).
Domasio, "Alzheimer's disease and related dementias," Cecil Textbook of Medicine, 20th edition, 2:1992-1996 (1996).
Dubois et al., "Research criteria for the diagnosis of Alzheimer's disease: revising the NINCDS-ADRDA criteria," Lancet Neurology, 6(8):734-736 (2007).
Dubois et al., "Revising the definition of Alzheimer's disease: a new lexicon," Lancet Neurology, 9(11):1118-27 (2010).
EESR for European Application No. 14774060.9, dated Aug. 17, 2016 (11 pages).
EESR for European Application No. 14775126.7, dated Sep. 14, 2016 (7 pages).
EESR for European Application No. 14775126.7, Dec. 15, 2016 (7 pages).
EESR for European Application No. 15809462.3, dated Nov. 29, 2017 (8 pages).
EESR for European Application No. 15849514.3, dated May 23, 2018 (7 pages).
EESR for European Application No. 16821920.2, dated Jan. 31, 2019 (12 pages).
EESR for European Application No. 16821924.4, dated Jan. 31, 2019 (12 pages).
EESR for European Application No. 16821926.9, dated Jan. 31, 2019 (10 pages).
Elbarbry et al., "Cyclosporine-induced changes in drug metabolizing enzymes in hyperlipemic rabbit kidneys could explain its toxicity," Xenobiotica, 40(11):772-781 (2010).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs 16: 2033-2052 (2010).
Festa et al., "Exploitation of cholane scaffold for the discovery of potent and selective farnesoid X receptor (FXR) and G-protein coupled bile acid receptor 1 (GP-BAR1) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12(4):279-287 (1991).
Grynkiewicz et at., "A new generation of Ca2+ indicators with greatly improved fluorescence properties," Journal of Biological Chemistry, 260(6):3440-3345 (1985).
Gunatilaka et al., "Bioactive ergost-5-ene-3 beta, 7 alpha-diol derivatives from *Pseudobersama mossambicensis*," Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Iida et al., "An improved method for the capillary gas chromatographic derivatization of polyhydroxylated steroids having tert-hydroxyl groups," Analytical Sciences, 19(9):1317-1321 (2003).
Iida et al., "Preparation of glycine-conjugated bile acids and their gas/liquid chromatographic analysis on an aluminum-clad flexible fused silica capillary column," Biomed Chromatography, 6(1):4-8 (1992).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jack et al., "Hypothetical model of dynamic biomarkers of the Alzheimer's pathological cascade," Lancet Neurology, 9(1):119-128 (2010).
Jack et al., "Introduction to the recommendations from the National Institute on Aging—Alzheimer's Association workgroups on diagnostic guidelines for Alzheimer's disease," Alzheimer's & Dementia, 7(3):257-62 (2011).
Jurman et al., "Visual identification of individual transfected cells for electrophysiology using antibody-coated beads," Biotechniques, 17(5):876-881 (1994).
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al., "NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Changes in human plasma levels of the brain specific oxysterol 24S-hydroxycholesterol during progression of multiple sclerosis," Neuroscience Letters, 331(3):163-166 (2002).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Litvan et al., "Diagnostic criteria for mild cognitive impairment in Parkinson's disease: Movement Disorder Society Task Force guidelines," Movement Disorders, 27(3):349-56 (2012).

(56) References Cited

OTHER PUBLICATIONS

Litvan et al., "MDS Task Force on mild cognitive impairment in Parkinson's disease: critical review of PD-MCI," Movement Disorders, 26(10):1814-1824 (2011).
Lutjohann et al., "Cholesterol homeostasis in human brain: evidence for an age-dependent flux of 24S-hydroxycholesterol from the brain into the circulation," PNAS, 93(18):9799-804 (1996).
Madau et al, Program No. 613.2/B87. 2009 Neuroscience Meeting Planner. Chicago, IL: Society for Neuroscience (2009) (3 pages).
Magyar et al., "Stereoselective reactions of (20R)-3,20-dihydroxy-(3',4'-dihydro-2'H-pyranyl)-5-pregnene derivatives form 27-nor-3,20,23,26-tetrahydroxy-cholesten-22-ones and related bromo ketones," Steroids, 69(1):35-42 (2004).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dhcr7(Δ3-5/T93M) mouse: a model of Smith-Lemli-Opitz syndrome," Biochemical Pharmacology, 86(1):43-55 (2013).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-1a,25-dihydroxyvitamin D3 and 24-nor-25¬hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Nagasaka et al., "Oxysterol changes along with cholesterol and vitamin D changes in adult phenylketonuric patients diagnosed by newborn mass-screening," Clinica Chimica Acta, 416:54-59 (2013).
Nasreddine et al., "The Montreal Cognitive Assessment, MoCA: a brief screening tool for mild cognitive impairment," Journal of the American Geriatrics Society, 53(4):695-699 (2005).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890) (2 pages).
Niemann-Pick overview [online] retrieved from the internet on Jul. 17, 2021 (URL: https://www.mayoclinic.org/diseases-conditions/niemann-pick/symptoms-causes/syc-20355887) (4 pages).
Olkkonen et al., "Oxysterols and their cellular effectors," Biomolecules, 2(1):76-103 (2012).
Papassotiropoulos, et al., "Plasma 24S-hydroxycholesterol a peripheral indicator of neuronal degeneration and potential state marker for Alzheimer's disease", NeuroReport 11(9): 1959-1962 (2000).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Aug. 14, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Dec. 11, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113 (2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Solomon, et al., "Plasma levels of 24S-hydroxycholesterol reflect brain volumes in patients without objective cognitive impairment but not in those with Alzheimer's disease", Neuroscience Letters 462(1): 89-93 (2009).
Stamp et al., "Plasma levels and therapeutic effect of 25-hydroxycholecalciferol in epileptic patients taking anticonvulsant drugs," British Medical Journal 4(5831): 9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).

(56) References Cited

OTHER PUBLICATIONS

Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron, 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zhou et al., "Properties of HERG channels stably expressed in HEK 293 cells studied at physiological temperature," Biophysical Journal, 74(1):230-241 (1998).
Zuliani et al., "Plasma 24S-hydroxycholesterol levels in elderly subjects with late onset Alzheimer's disease or vascular dementia: a case-control study," BMC Neurology 11(121): 1-8 (2011).
U.S. Appl. No. 14/343,603, filed Nov. 25, 2014, Ravindra B. Upasani et al., Abandoned.
U.S. Appl. No. 14/775,401, filed Sep. 11, 2015, Kiran Reddy et al., Abandoned.
U.S. Appl. No. 14/775,678, filed Sep. 12, 2015, Gabriel Martinez Botella et al., Abandoned.
U.S. Appl. No. 15/319,504, filed Dec. 16, 2016, Boyd L. Harrison et al., Issued.
U.S. Appl. No. 15/517,886, filed Apr. 7, 2017, Michael C. Quirk et al., Abandoned.
U.S. Appl. No. 15/588,305, filed May 5, 2017, Gabriel Martinez Botella et al., Abandoned.
U.S. Appl. No. 15/742,422, filed Jan. 5, 2018, Francesco G. Salituro et al., Issued.
U.S. Appl. No. 15/742,424, filed Jan. 5, 2018, Francesco G. Salituro et al., Issued.
U.S. Appl. No. 15/742,425, filed Jan. 5, 2018, Francesco G. Salituro et al., Issued.
U.S. Appl. No. 15/917,263, filed Mar. 9, 2018, Gabriel Martinez Botella et al., Issued.
U.S. Appl. No. 15/917,272, filed Mar. 9, 2018, Gabriel Martinez Botella et al., Abandoned.
U.S. Appl. No. 16/028,790, filed Jul. 6, 2018, Boyd L. Harrison et al., Issued.
U.S. Appl. No. 16/089,896, filed Sep. 28, 2018, Albert Jean Robichaud et al., Abandoned.
U.S. Appl. No. 16/099,122, filed Nov. 5, 2018, Gabriel Martinez Botella et al., Issued.
U.S. Appl. No. 16/114,791, filed Aug. 28, 2018, Ravindra B. Upasani et al., Issued.
U.S. Appl. No. 16/227,013, filed Dec. 20, 2018, Gabriel Martinez Botella et al., Issued.
U.S. Appl. No. 16/227,099, filed Dec. 20, 2018, Francesco G. Salituro et al., Issued.
U.S. Appl. No. 16/315,250, filed Jan. 4, 2019, Francesco G. Salituro et al., Issued.
U.S. Appl. No. 16/338,315, filed Mar. 29, 2019, Francesco G. Salituro et al., Issued.
U.S. Appl. No. 16/343,235, filed Apr. 18, 2019, Francesco G. Salituro et al., Issued.
U.S. Appl. No. 16/343,238, filed Apr. 18, 2019, Francesco G. Salituro et al., Issued.
U.S. Appl. No. 16/879,460, filed May 20, 2020, Francesco G. Salituro et al., Abandoned.
U.S. Appl. No. 16/902,730, filed Jun. 16, 2020, Boyd L. Harrison et al., Abandoned.
U.S. Appl. No. 16/930,047, filed Jul. 15, 2020, Gabriel Martinez Botella et al., Issued.
U.S. Appl. No. 16/938,348, filed Jul. 24, 2020, James J. Doherty, Abandoned.
U.S. Appl. No. 16/942,235, filed Jul. 29, 2020, Ravindra B. Upasani et al., Abandoned.
U.S. Appl. No. 16/942,245, filed Jul. 29, 2020, Francesco G. Salituro et al., Pending.
U.S. Appl. No. 16/943,649, filed Jul. 30, 2020, Francesco G. Salituro et al., Issued.
U.S. Appl. No. 17/242,860, filed Apr. 28, 2021, Albert Jean Robichaud et al., Pending.
U.S. Appl. No. 17/386,364, filed Jul. 27, 2021, Francesco G. Salituro et al., Issued.
U.S. Appl. No. 17/395,155, filed Aug. 5, 2021, Francesco G. Salituro et al., Pending.
U.S. Appl. No. 17/396,034, filed Aug. 6, 2021, Francesco G. Salituro et al., Allowed.
U.S. Appl. No. 17/476,153, filed Sep. 15, 2021, Francesco G. Salituro et al., Pending.
U.S. Appl. No. 17/707,303, filed Mar. 29, 2022, Ravindra B. Upasani et al., Pending.
U.S. Appl. No. 17/749,976, filed May 20, 2022, Francesco G. Salituro et al., Pending.
U.S. Appl. No. 17/860,816, filed Jul. 8, 2022, Gabriel Martinez Botella et al., Pending.
U.S. Appl. No. 17/947,844, filed Sep. 19, 2022, Michael C. Quirk et al., Pending.
U.S. Appl. No. 18/077,031, filed Dec. 7, 2022, James J. Doherty, Pending.
U.S. Appl. No. 18/106,073, filed Feb. 6, 2023, Francesco G. Salituro et al., Pending.
U.S. Appl. No. 18/216,057, filed Jun. 29, 2023, Francesco G. Salituro et al., Pending.

OXYSTEROLS AND METHODS OF USE THEREOF

RELATED APPLICATIONS

This application is a Continuation application of U.S. patent application Ser. No. 16/902,730, filed Jun. 16, 2020, which is a Continuation application of U.S. patent application Ser. No. 16/028,790, filed Jul. 6, 2018, which is a Continuation application of U.S. National Phase application Ser. No. 15/319,504 filed Dec. 16, 2016, which is a National Phase application under 35 U.S.C. § 371 of International Application No. PCT/US2015/036510 filed Jun. 18, 2015, which claims priority to and the benefit of U.S. Provisional Application No. 62/014,014 filed Jun. 18, 2014, and U.S. Provisional Application No. 62/107,236 filed Jan. 23, 2015. The contents of each of the foregoing applications are hereby incorporated by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are derived from cholesterol and have been shown to potently and selectively modulate NMDA receptor function. New and improved oxysterols are needed that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols. Further provided are pharmaceutical compositions comprising the compounds of the present invention, and methods of their use and treatment.

In one aspect, provided herein are compounds according to Formula (I):

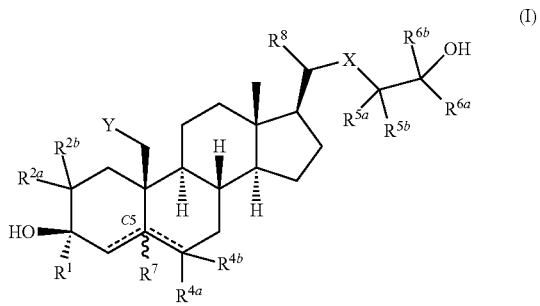

or a pharmaceutically acceptable salt thereof, wherein: $R^1$ is hydrogen, $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —$OR^A$, or —$NR^B R^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); each of $R^{4a}$ and $R^{4b}$ is independently absent, hydrogen, $C_1$-$C_6$ alkyl, or halo; X is —$C(R^X)_2$— or —O—, wherein $R^X$ is independently hydrogen, halo, or one $R^X$ group and $R^{5b}$ are joined to form a double bond; Y is —$OR^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, —$C(O)NR^B R^C$, or —$S(O)_2 R^D$; each instance of $R^{5a}$ and $R^{5b}$ is independently hydrogen, halo, or $C_1$-$C_6$ alkyl; each of $R^{6a}$ and $R^{6b}$ is independently hydrogen, $C_1$-$C_6$ alkyl, $C_2$-$C_6$ alkenyl, $C_2$-$C_6$ alkynyl, carbocyclyl, heterocyclyl, aryl, or heteroaryl, or $R^{6a}$ and R b, taken together with the carbon atom to which they are attached, form a ring (e.g., a 3-6-membered ring, e.g. a 4-6-membered ring containing one heteroatom); or $R^{5a}$ and $R^{6a}$, together with the carbon atoms to which they are attached, form a ring (e.g., a 3-6-membered ring, e.g. a 4-6-membered ring containing one heteroatom); and $R^7$ is absent or hydrogen in the alpha configuration; $R^8$ is hydrogen, halo, $C_{1-6}$alkyl, carbocyclyl, or —$OR^A$; ═══ represents a single or double bond, wherein when one ─── is a double bond, the other ═══ is a single bond; wherein when the ═══ between —$CR^7$ and —$CR^{4a}R^{4b}$ is a double bond, then one of $R^{4a}$ or $R^{4b}$ is absent; and when one of the ═══ is a double bond, $R^7$ is absent; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring; and $R^D$ is hydrogen, $C_1$-$C_6$ alkyl, carbocyclyl, heterocyclyl, aryl, or heteroaryl.

In another aspect, provided are pharmaceutical compositions comprising a compound of Formula (I), or a pharmaceutically acceptable salt thereof, and a pharmaceutically acceptable excipient.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and*

Physics, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, *Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_2$-10 alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH═CH—) and propenylene (e.g., —CH═CHCH$_2$—, —CH$_2$—CH═CH—). Exemplary substituted alkenylene groups, e.g., substituted with one or more alkyl (methyl) groups, include but are not limited to, substituted ethylene (—C(CH$_3$)═CH—, —CH═C(CH$_3$)—), substituted propylene (e.g., —C(CH$_3$)═CHCH$_2$—, —CH═C(CH$_3$)CH$_2$—, —CH═CHCH(CH$_3$)—, —CH═CHC(CH$_3$)$_2$—, —CH(CH$_3$)—CH═CH—, —C(CH$_3$)$_2$—CH═CH—, —CH$_2$—C(CH$_3$)═CH—, —CH$_2$—CH═C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the het-eroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"'Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

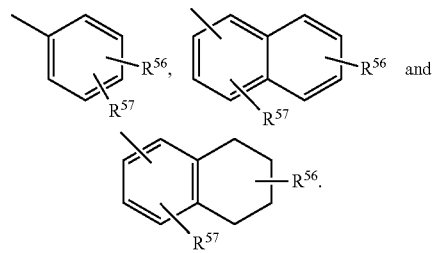

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

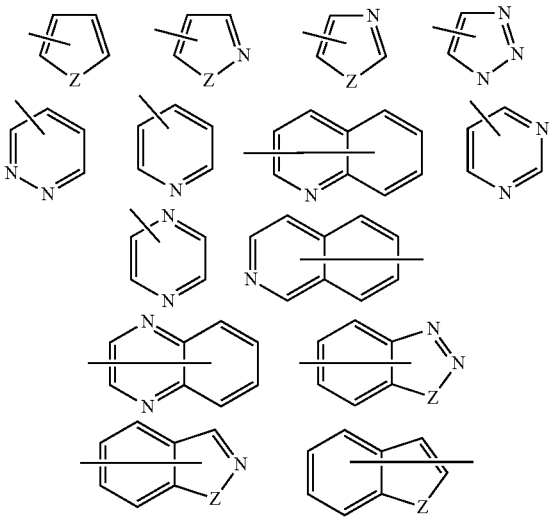

wherein each Z is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)$CH_3$), cyclohexylcarbonyl, cyclohexylmethylcarbonyl, benzoyl (—C(=O)Ph), benzylcarbonyl (—C(=O)$CH_2$Ph), C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}$C(O)$R^{23}$, where each instance of $R^{22}$ and $R^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}$C(O)—$C_1$-$C_8$ alkyl, —$NR^{24}$C(O)—$(CH_2)_t$($C_6$-$C_{10}$ aryl), —$NR^{24}$C(O)—$(CH_2)_t$(5-10 membered heteroaryl), —$NR^{24}$C(O)—$(CH_2)_t$($C_3$-$C_{10}$ cycloalkyl), and —$NR^{24}$C(O)—$(CH_2)_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$-$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —C(O)$NH_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, —C(O) $NR^{64}$—$C_1$-$C_8$ alkyl, —C(O)$NR^{64}$—$(CH_2)_t(C_6$-$C_{10}$ aryl), —C(O)$NR^{64}$—$(CH_2)_t$(5-10 membered heteroaryl), —C(O)$NR^{64}$—$(CH_2)_t$($C_3$-$C_{10}$ cycloalkyl), and —C(O)$NR^{64}$—$(CH_2)_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C=C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^c$)R$^{bb}$, —SH, —SR—, —SSR$^{cc}$, —C(=O)R$^{aa}$, —CO$_2$H, —CHO, —C(OR$^{cc}$), —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{cc}$)$_2$, —OP(=O)(R$^{aa}$), —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$), —NR$^{bb}$P(=O)(NR$^{bb}$)$_2$, —P(R$^{C}$), —P(R$^{C}$)$_3$, —OP(R$^{cc}$)$_2$, —OP(R$^{cc}$)$_3$, —B(R$^{aa}$)$_2$, —B(OR$^{cc}$), —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^a$, —N(R$^{cc}$), —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$), —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ee}$C(=O)R$^{ee}$, —NR$^{ee}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ee}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^f$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^f$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$), —CN, —C(=O)R$^{aa}$, —C(=O)N(R$^{cc}$), —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$), —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

[1] As generally described herein, the present invention provides 19-substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

Compounds

In one aspect, provided herein are compounds according to Formula (I):

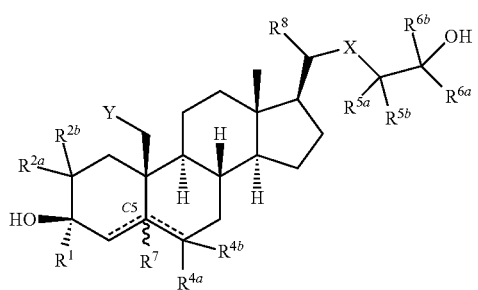

or a pharmaceutically acceptable salt thereof, wherein: $R^1$ is hydrogen, $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —$OR^A$, or —$NR^B R^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); each of $R^{4a}$ and $R^{4b}$ is independently absent, hydrogen, $C_1$-$C_6$ alkyl, or halo; X is —$C(R^X)_2$— or —O—, wherein $R^X$ is independently hydrogen, halogen, or one $R^X$ group and $R^{5b}$ are joined to form a double bond; Y is —$OR^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, —$C(O)NR^B R^C$, or —$S(O)_2 R^D$; each instance of $R^{5a}$ and $R^{5b}$ is independently hydrogen, halo, or $C_1$-$C_6$ alkyl; each of $R^{6a}$ and $R^b$ is independently hydrogen, $C_1$-$C_6$ alkyl, $C_2$-$C_6$ alkenyl, $C_2$-$C_6$ alkynyl, carbocyclyl, heterocyclyl, aryl, or heteroaryl, or $R^{6a}$ and $R^{6b}$, taken together with the carbon atom to which they are attached, form a ring (e.g., a 3-6-membered ring, e.g. a 4-6-membered ring containing one heteroatom); or $R^{5a}$ and $R^{6a}$, together with the carbon atoms to which they are attached, form a ring (e.g., a 3-6-membered ring, e.g. a 4-6-membered ring containing one heteroatom); and $R^7$ is absent or hydrogen in the alpha configuration; $R^8$ is hydrogen, halo, $C_{1-6}$alkyl, carbocyclyl, or —$OR^A$; ═══ represents a single or double bond, wherein when one ═══ is a double bond, the other ═══ is a single bond; wherein when the ═══ between —$CR^7$ and —$CR^{4a}R^{4b}$ is a double bond, then one of $R^{4a}$ or $R^{4b}$ is absent; and when one of the ═══ is a double bond, $R^7$ is absent; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring; and $R^D$ is hydrogen, $C_1$-$C_6$ alkyl, carbocyclyl, heterocyclyl, aryl, or heteroaryl.

In certain embodiments, $R^1$ is hydrogen. In certain embodiments, $R^1$ is unsubstituted $C_{1-3}$ alkyl. In certain embodiments, $R^1$ is —$CH_3$, —$CH_2CH_3$, or —$CH_2CH_2CH_3$. In certain embodiments, $R^1$ is substituted $C_{1-3}$ alkyl. In certain embodiments, $R^1$ is —$CF_3$ or —$CH_2OCH_3$.

In certain embodiments, $R^{2a}$ is hydrogen. In certain embodiments, $R^{2b}$ is hydrogen. In certain embodiments, $R^{2a}$ or $R^{2b}$ is hydrogen. In certain embodiments, $R^{2a}$ and $R^{2b}$ is hydrogen.

In certain embodiments, $R^{4a}$ is hydrogen. In certain embodiments, $R^{4b}$ is hydrogen. In certain embodiments, $R^{4a}$ or $R^{4b}$ is hydrogen. In certain embodiments, $R^{4a}$ and $R^{4b}$ is hydrogen.

In certain embodiments, X is —$CH_2$—.

In certain embodiments, $R^8$ is substituted or unsubstituted $C_{1-3}$ alkyl. In certain embodiments, $R^8$ is —$CH_3$.

In certain embodiments, the ═══ between —$CR^7$ and —$CR^{4a}R^{4b}$ is a double bond, and one of $R^{4a}$ or $R^{4b}$ is absent.

In certain embodiments ═══ is a single bond, and $R^7$ is hydrogen in the alpha ═══ configuration.

In certain embodiments, the compound of Formula (I) is a compound of Formula (I-A) or (I-B):

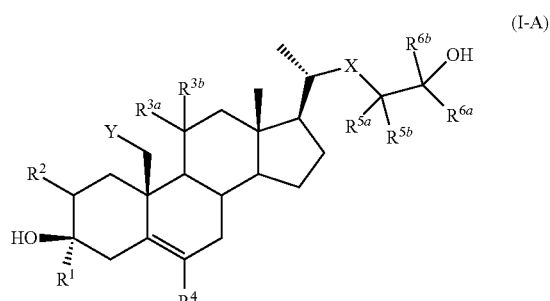

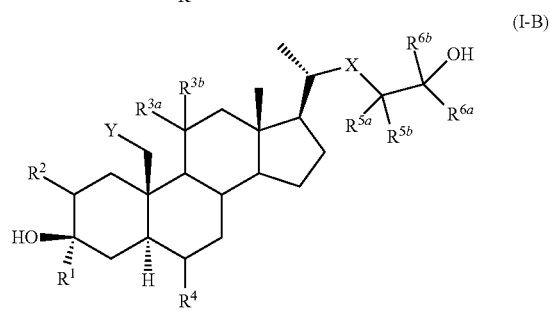

or a pharmaceutically acceptable salts thereof.

In certain embodiments, the compound of Formula (I) is a compound of Formula (II):

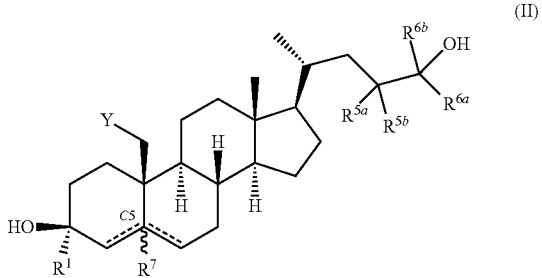

(II)

or a pharmaceutically acceptable salt thereof.

In certain embodiments, the compound of Formula (II) is a compound of Formula (II-A):

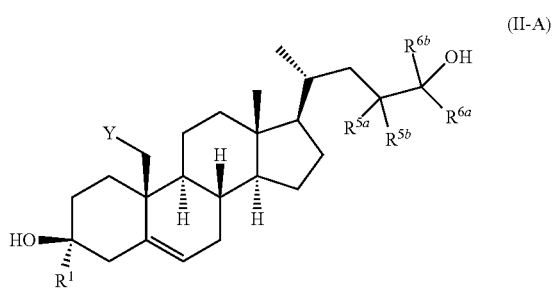

(II-A)

or a pharmaceutically acceptable salt thereof.

In certain embodiments, the compound of Formula (II-A) is a compound of Formula (III):

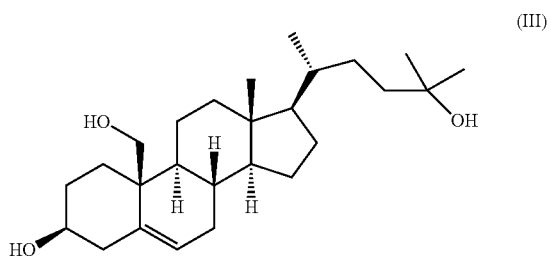

(III)

or a pharmaceutically acceptable salt thereof.

In certain embodiments, the compound of Formula (II) is a compound of Formula (II-B):

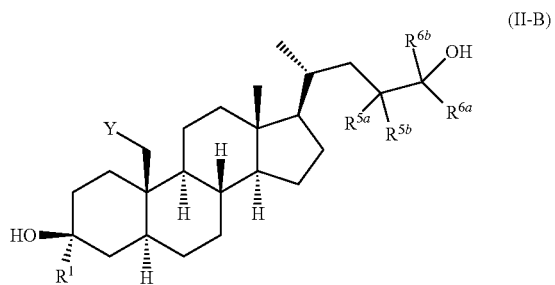

(II-B)

or a pharmaceutically acceptable salt thereof.

In certain embodiments, $R^{5a}$ or $R^{5b}$ is hydrogen. In certain embodiments, $R^{5a}$ and $R^{5b}$ are both hydrogen.

In certain embodiments, $R^{6a}$ is a substituted or unsubstituted $C_{1-3}$ alkyl (e.g., $C_{1-3}$ haloalkyl). In certain embodiments, $R^{6a}$ is —$CH_3$ or —$CH_2CH_3$. In certain embodiments, $R^{6a}$ is a substituted or unsubstituted $C_{2-4}$ alkyl, substituted or unsubstituted $C_{2-3}$ alkenyl, substituted or unsubstituted $C_{2-3}$ alkynyl, or substituted or unsubstituted carbocyclyl.

In certain embodiments, $R^{6b}$ is substituted or unsubstituted $C_{1-3}$ alkyl (e.g., $C_{1-3}$ haloalkyl). In certain embodiments, $R^{6b}$ is —$CH_3$ or —$CH_2CH_3$. In certain embodiments, $R^{6b}$ is hydrogen. In certain embodiments, $R^{6b}$ is —$CH_3$ or —$CF_3$.

In certain embodiments, $R^{6a}$ or $R^{6b}$ is hydrogen. In certain embodiments, $R^{6a}$ and $R^{6b}$ are both hydrogen.

In certain embodiments, $R^{6a}$ is hydrogen and $R^{6b}$ is substituted or unsubstituted $C_{1-3}$ alkyl (e.g., —$CH_3$, —$CH_2CH_3$; $C_{1-3}$ haloalkyl (e.g., —$CF_3$)).

In certain embodiments, $R^{6a}$ and $R^b$ are both —$CH_3$. In certain embodiments, $R^{6a}$ is —$CH_3$ and $R^{6b}$ is —$CH_2CH_3$. In certain embodiments, $R^{6a}$ and $R^{6b}$, taken together with the atom to which they are attached, form a ring. In certain embodiments, the ring is a 3-membered ring.

In certain embodiments, $R^1$ is hydrogen or $C_{1-3}$ alkyl, $R^{6a}$ is substituted or unsubstituted $C_{1-3}$ alkyl (e.g., $C_{1-3}$ haloalkyl), substituted or unsubstituted $C_{2-3}$ alkenyl, substituted or unsubstituted $C_{2-3}$ alkynyl, or substituted or unsubstituted carbocyclyl, and $R^{6b}$ is —$CH_3$.

In certain embodiments, $R^{6a}$ is selected from the group consisting of substituted or unsubstituted $C_{1-3}$ alkyl (e.g., $C_{1-3}$ haloalkyl), unsubstituted $C_{2-3}$ alkenyl, unsubstituted $C_{2-3}$ alkynyl, or unsubstituted carbocyclyl. In certain embodiments, $R^{6a}$ is selected from a substituted or unsubstituted $C_{1-3}$ alkyl (e.g., $C_{1-3}$ haloalkyl).

In certain embodiments, $R^1$ is —$CH_3$ or —$CH_2CH_3$ and $R^{6b}$ is —$CH_3$ or —$CF_3$.

In certain embodiments, $R^Y$ is substituted or unsubstituted $C_{1-3}$ alkyl (e.g., $C_{1-3}$ haloalkyl). In certain embodiments, $R^Y$ is substituted or unsubstituted heterocyclyl. In certain embodiments, $R^Y$ is —$CH_3$ or —$CH_2CH_3$. In certain embodiments, $R^Y$ is —$CF_3$.

In certain embodiments, the compound of Formula (I) is:

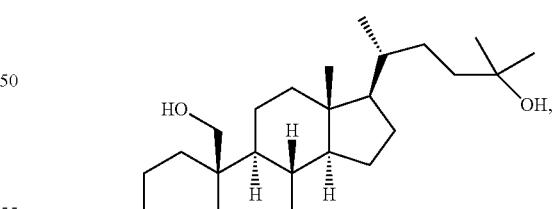

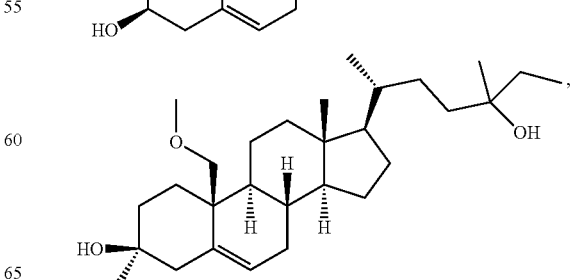

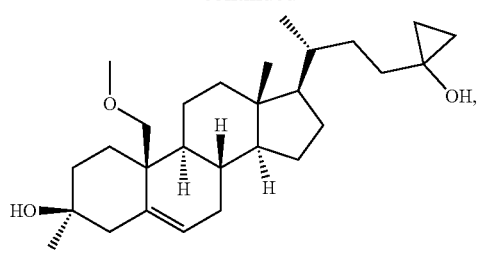
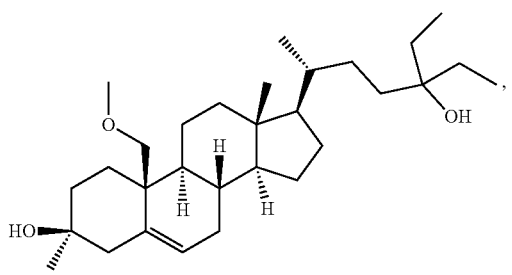
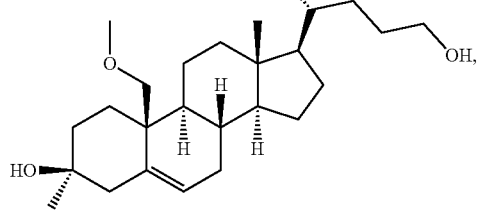
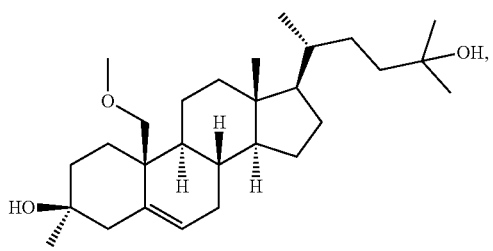
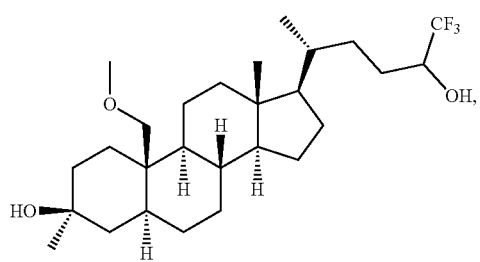
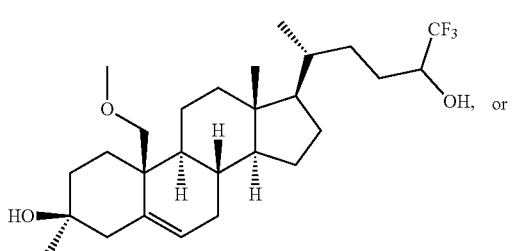
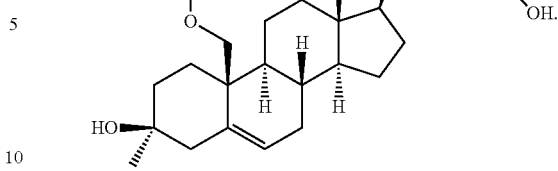

or a pharmaceutically acceptable salt thereof.

In one aspect, the present invention provides pharmaceutical compositions comprising a compound as described herein, e.g., a compound of Formula (I), or a pharmaceutically acceptable salt or pharmaceutically acceptable carrier thereof.

In one aspect, the present invention provides a method of inducing sedation or anesthesia comprising administering to a subject an effective amount of a compound as described herein, e.g., a compound of Formula (I), or a pharmaceutically acceptable salt thereof, or a pharmaceutically acceptable carrier thereof.

In one aspect, provided herein is a method for treating or preventing a disorder described herein, comprising administering to a subject in need thereof an effective amount of a compound as described herein, e.g., a compound of Formula (I), or pharmaceutically acceptable salt thereof, or pharmaceutical composition thereof. In some embodiments, the disorder is a NMDA-mediated disorder. In some embodiments, the disorder is a disorder mediated by NMDA, e.g., a disorder which benefits from treatment with a NMDA modulator. In some embodiments, the disorder is cancer. In some embodiments, the disorder is diabetes. In some embodiments, the disorder is a sterol synthesis disorder. In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In one aspect, provided herein is a method for treating or preventing a CNS-related condition comprising administering to a subject in need thereof an effective amount of a compound as described herein, e.g., a compound of Formula (I), or a pharmaceutically acceptable salt thereof, or a pharmaceutically acceptable carrier thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

Pharmaceutical Compositions

In another aspect, the invention provides a pharmaceutical composition comprising a pharmaceutically acceptable carrier and a effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (I) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-p-cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (I), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (I), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula (I), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula (I), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (I), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (I), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (I), or pharmaceutically acceptable salt thereof, may act as a negative allosteric modulator (NAM) of NMDA, and inhibit NMDA receptor function. In certain embodiments, the present invention, e.g., a compound of Formula (I), or pharmaceutically acceptable salt thereof, may act as positive allosteric modulators (PAM) of NMDA, and potentiate NMDA receptor function. In certain embodiments, the compound of Formula (I), or pharmaceutically acceptable salt thereof, modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

Exemplary conditions related to NMDA-modulation includes, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (I), or pharmaceutically acceptable salt thereof, can be used to induce sedation or anesthesia. In certain embodiments, the compound of Formula (I), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, and tinnitus.

In another aspect, provided is a method of treating or preventing brain excitability in a subject susceptible to or afflicted with a condition associated with brain excitability, comprising administering to the subject an effective amount of a compound of the present invention, e.g., a compound of Formula (I), or a pharmaceutically acceptable salt thereof.

In yet another aspect, the present invention provides a combination of a compound of the present invention, e.g., a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

EXAMPLES

[2] In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of Compound 1

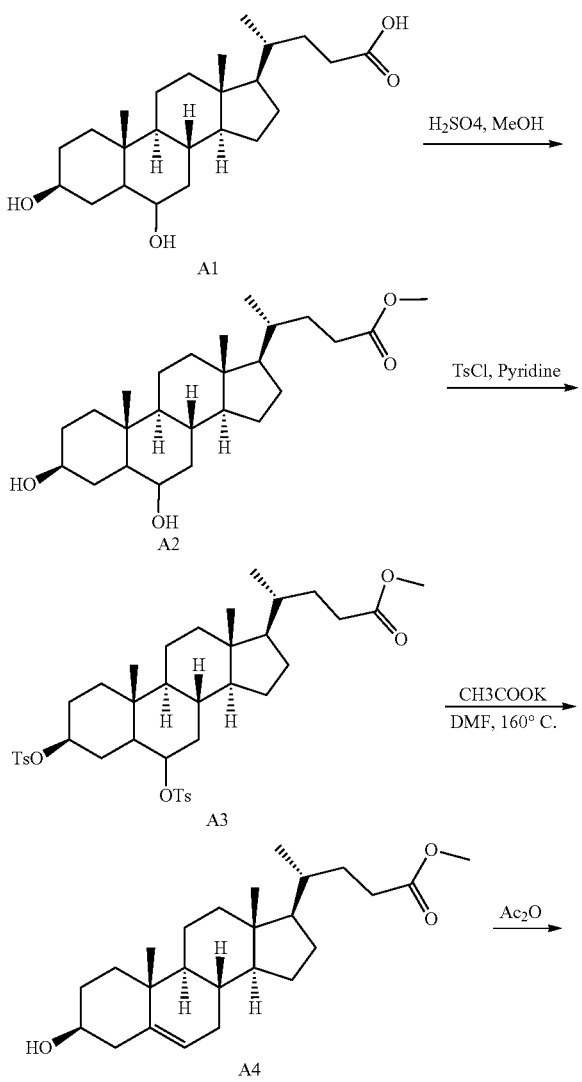

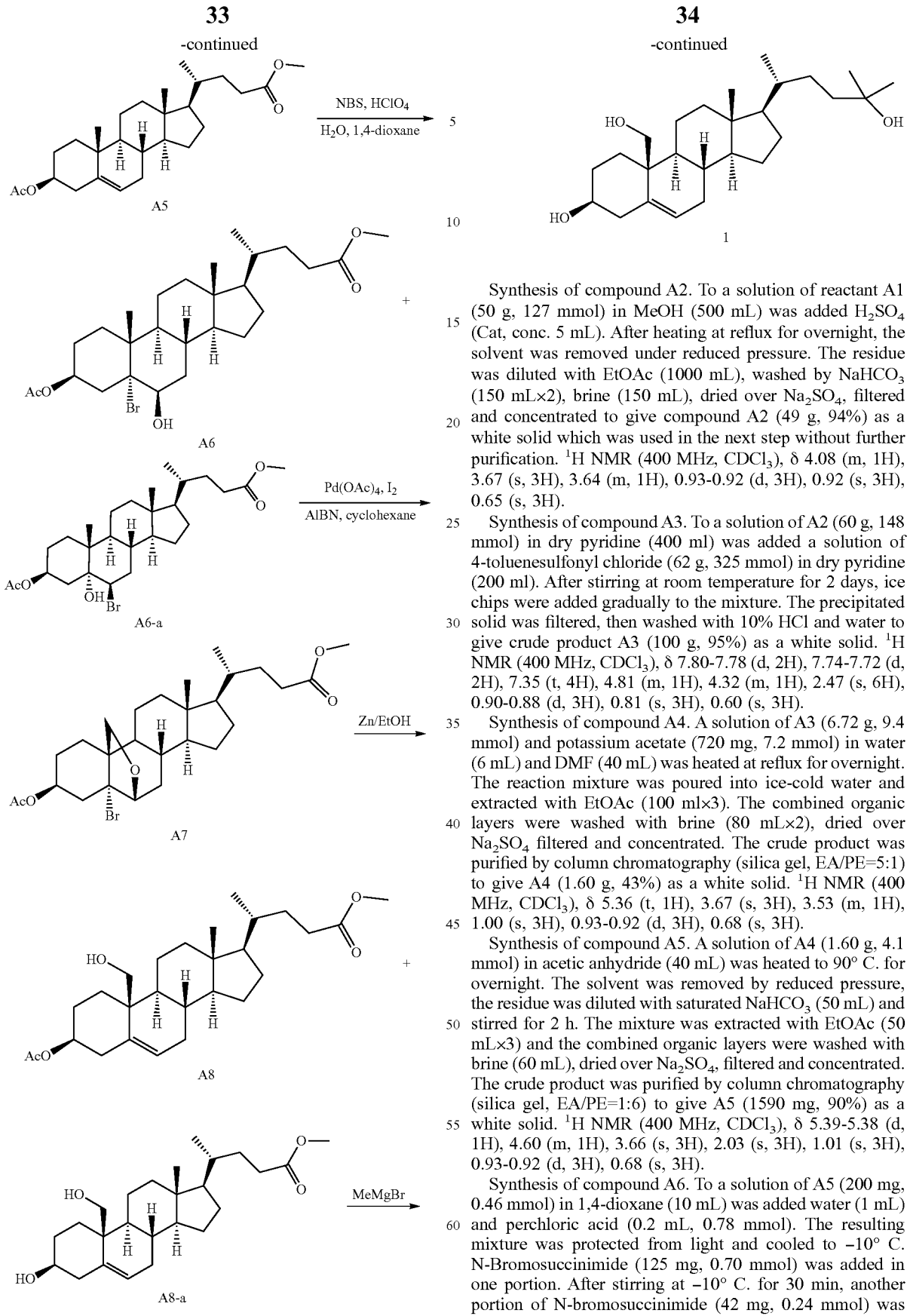

Synthesis of compound A2. To a solution of reactant A1 (50 g, 127 mmol) in MeOH (500 mL) was added $H_2SO_4$ (Cat, conc. 5 mL). After heating at reflux for overnight, the solvent was removed under reduced pressure. The residue was diluted with EtOAc (1000 mL), washed by $NaHCO_3$ (150 mL×2), brine (150 mL), dried over $Na_2SO_4$, filtered and concentrated to give compound A2 (49 g, 94%) as a white solid which was used in the next step without further purification. $^1$H NMR (400 MHz, $CDCl_3$), δ 4.08 (m, 1H), 3.67 (s, 3H), 3.64 (m, 1H), 0.93-0.92 (d, 3H), 0.92 (s, 3H), 0.65 (s, 3H).

Synthesis of compound A3. To a solution of A2 (60 g, 148 mmol) in dry pyridine (400 ml) was added a solution of 4-toluenesulfonyl chloride (62 g, 325 mmol) in dry pyridine (200 ml). After stirring at room temperature for 2 days, ice chips were added gradually to the mixture. The precipitated solid was filtered, then washed with 10% HCl and water to give crude product A3 (100 g, 95%) as a white solid. $^1$H NMR (400 MHz, $CDCl_3$), δ 7.80-7.78 (d, 2H), 7.74-7.72 (d, 2H), 7.35 (t, 4H), 4.81 (m, 1H), 4.32 (m, 1H), 2.47 (s, 6H), 0.90-0.88 (d, 3H), 0.81 (s, 3H), 0.60 (s, 3H).

Synthesis of compound A4. A solution of A3 (6.72 g, 9.4 mmol) and potassium acetate (720 mg, 7.2 mmol) in water (6 mL) and DMF (40 mL) was heated at reflux for overnight. The reaction mixture was poured into ice-cold water and extracted with EtOAc (100 ml×3). The combined organic layers were washed with brine (80 mL×2), dried over $Na_2SO_4$ filtered and concentrated. The crude product was purified by column chromatography (silica gel, EA/PE=5:1) to give A4 (1.60 g, 43%) as a white solid. $^1$H NMR (400 MHz, $CDCl_3$), δ 5.36 (t, 1H), 3.67 (s, 3H), 3.53 (m, 1H), 1.00 (s, 3H), 0.93-0.92 (d, 3H), 0.68 (s, 3H).

Synthesis of compound A5. A solution of A4 (1.60 g, 4.1 mmol) in acetic anhydride (40 mL) was heated to 90° C. for overnight. The solvent was removed by reduced pressure, the residue was diluted with saturated $NaHCO_3$ (50 mL) and stirred for 2 h. The mixture was extracted with EtOAc (50 mL×3) and the combined organic layers were washed with brine (60 mL), dried over $Na_2SO_4$, filtered and concentrated. The crude product was purified by column chromatography (silica gel, EA/PE=1:6) to give A5 (1590 mg, 90%) as a white solid. $^1$H NMR (400 MHz, $CDCl_3$), δ 5.39-5.38 (d, 1H), 4.60 (m, 1H), 3.66 (s, 3H), 2.03 (s, 3H), 1.01 (s, 3H), 0.93-0.92 (d, 3H), 0.68 (s, 3H).

Synthesis of compound A6. To a solution of A5 (200 mg, 0.46 mmol) in 1,4-dioxane (10 mL) was added water (1 mL) and perchloric acid (0.2 mL, 0.78 mmol). The resulting mixture was protected from light and cooled to −10° C. N-Bromosuccinimide (125 mg, 0.70 mmol) was added in one portion. After stirring at −10° C. for 30 min, another portion of N-bromosuccinimide (42 mg, 0.24 mmol) was added. The reaction mixture was stirred until TLC showed no SM. The reaction mixture was quenched with 0.1M of $Na_2S_2O_5$ solution (40 mL) and extracted with EtOAc (40 mL×3). The combined organic layers were dried over Na$_2$SO$_4$, filtered and concentrated. The residue was purified by column chromatography (PE:EA 10:1, 5:1) to afford A6 (100 mg, 42%) and A6-a (50 mg, 21%) as a white solid. A6 $^1$H NMR (400 MHz, CDCl$_3$), δ 5.09 (m, 1H), 3.98 (s, 1H), 3.67 (s, 3H), 2.06 (s, 3H), 1.36 (s, 3H), 0.94-0.92 (d, 3H), 0.72 (s, 3H); A6-a $^1$H NMR (400 MHz, CDCl$_3$), δ 5.49 (m, 1H), 4.2 (s, 1H), 2.04 (s, 3H), 1.33 (s, 3H), 0.93-0.91 (d, 3H), 0.68 (s, 3H).

Synthesis of compound A7. A solution of Pd(OAc)$_4$ (1.14 g, 3.32 mmol) and I$_2$ (170 mg, 0.67 mmol) in cyclohexane (60 mL) was heated to reflux for 10 min. Then compound A6 (700 mg, 1.33 mmol) and AIBN (10 mg, 0.08 mmol) were added and the resulting mixture was refluxed for overnight. The reaction mixture was allowed to cool to room temperature, filtered over a plug of celite and washed with EtOAc (100 mL). The organic layer was washed with a solution of 10% sodium metabisulfite (40 mL×2), dried over Na$_2$SO$_4$, filtered and concentrated. The residue was purified by column chromatography (silica gel, EA/PE=1:5) to give A7 (500 mg, 83%) as a white solid. $^1$H NMR (400 MHz, CDCl$_3$), δ 5.21 (m, 1H), 4.07-4.06 (d, 1H), 3.94-3.92 (d, 1H), 3.76-3.74 (d, 1H), 3.67 (s, 3H), 2.04 (s, 3H), 0.92-0.91 (d, 3H), 0.70 (s, 3H).

Synthesis of compound A8. To a solution of A7 (500 mg, 0.95 mmol) in EtOH (40 mL) was added Zn (620 mg, 9.5 mmol), the resulting solution was heated to reflux for 4 h. The reaction mixture was allowed to cool to room temperature, filtered over a plug of celite, washed with EtOAc and concentrated. The residue was purified by column chromatography (silica gel, EA/PE=5:1) to give A8 (310 mg, 72%) as a white solid and A8-a (80 mg, 17%) as a white solid. A8 $^1$H NMR (400 MHz, CDCl$_3$), δ 5.78 (t, 1H), 4.66 (m, 1H), 3.86-3.83 (d, 1H), 3.67 (s, 3H), 3.64-3.61 (d, 1H), 2.05 (s, 3H), 0.94-0.93 (d, 3H), 0.74 (s, 3H). A8-a $^1$H NMR (400 MHz, CDCl3), δ 5.75 (m, 1H), 3.84-3.81 (d, 1H), 3.67 (s, 3H), 3.62-3.60 (d, 1H), 0.94-0.92 (d, 3H), 0.74 (s, 3H).

Synthesis of compound 1. To a solution of A8-a (70 mg, 0.17 mmol) in THF (5 mL) was added MeMgBr (2 mL, 1M in THF) dropwise. After stirring at room temperature overnight, the mixture was quenched with water (20 mL) and extracted with EtOAc (15 mL×3). The combined organic layers were washed with brine, dried over Na$_2$SO$_4$, filtered and concentrated. The residue was purified by column chromatography (silica gel, EA:PE=1:1) to give 1 (20 mg, 30%) as a white solid. $^1$H NMR (400 MHz, CD$_3$OD), δ 5.62-5.61 (d, 1H), 3.85-3.82 (d, 1H), 3.59-3.56 (d, 1H), 1.17 (s, 3H), 3.45 (m, 1H), 1.16 (s, 3H), 0.97-0.96 (d, 3H), 0.78 (s, 3H).

Example 2. Synthesis of Compound 2

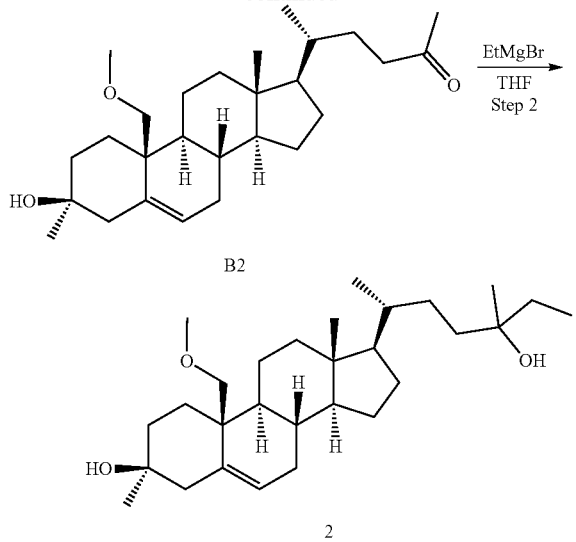

Synthesis of compound B2. To a solution of B1 (140 mg, 0.334 mmol) in DCM (5 mL) was added silica gel (100 mg) and PCC (107 mg, 0.5 mmol). The mixture was stirred at 25° C. for 16 hours. TLC (PE:EA=3:1) showed the starting material was consumed completely. The reaction mixture was filtered, and the filtrate was concentrated. The residue was purified by column chromatography on silica gel (PE: EA=10:1) to give B2 (120 mg, 86.3%) as white solid. LCMS Rt=1.157 min in 2 min chromatography, 30-90AB, purity 100%, MS ESI calcd. for C27H45O3 [M+H]$^+$ 417, found 399 ([M+H−18]$^+$).

Synthesis of compound 2. To a solution of B2 (140 mg, 0.336 mmol) in dry THF (5 mL) at 0° C. under N$_2$ was added EtMgBr (3 M in diethyl ether, 0.56 mL, 1.67 mmol) dropwise. The mixture was warmed to 25° C. and stirred for 16 hours. LCMS showed the starting material was consumed completely. The reaction mixture was quenched with aqueous NH$_4$Cl (10 mL), extracted with EtOAc (10 mL*3). The combined organic layers were dried over anhydrous sodium sulfate, filtered and concentrated. The residue was purified by prep. HPLC to give 2 (3 mg, 2%) as white solid. $^1$H NMR (400 MHz, CDCl$_3$) δ=5.57 (d, J=5.02 Hz, 1H), 3.59 (d, J=10.04 Hz, 1H), 3.26-3.32 (m, 4H), 2.47 (d, J=13.05 Hz, 1H), 1.61-2.08 (m, 10H), 1.24-1.49 (m, 9H), 1.05-1.17 (m, 10H), 0.74-1.03 (m, 11H), 0.71 (s, 3H). LCMS Rt=1.239 min in 2 min chromatography, 30-90AB, purity 100%, MS ESI calcd. for C$_{29}$H$_{51}$O$_3$[M+H]$^+$ 447, found 411 ([M+H−36]$^+$).

Example 3. Synthesis of Compounds 3 and 4

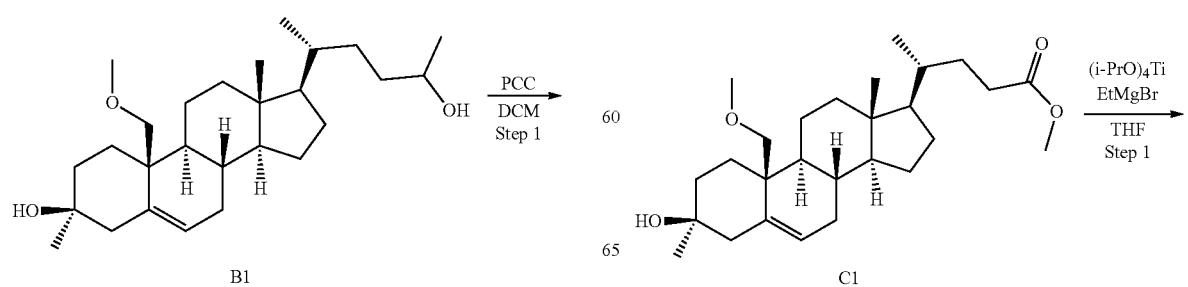

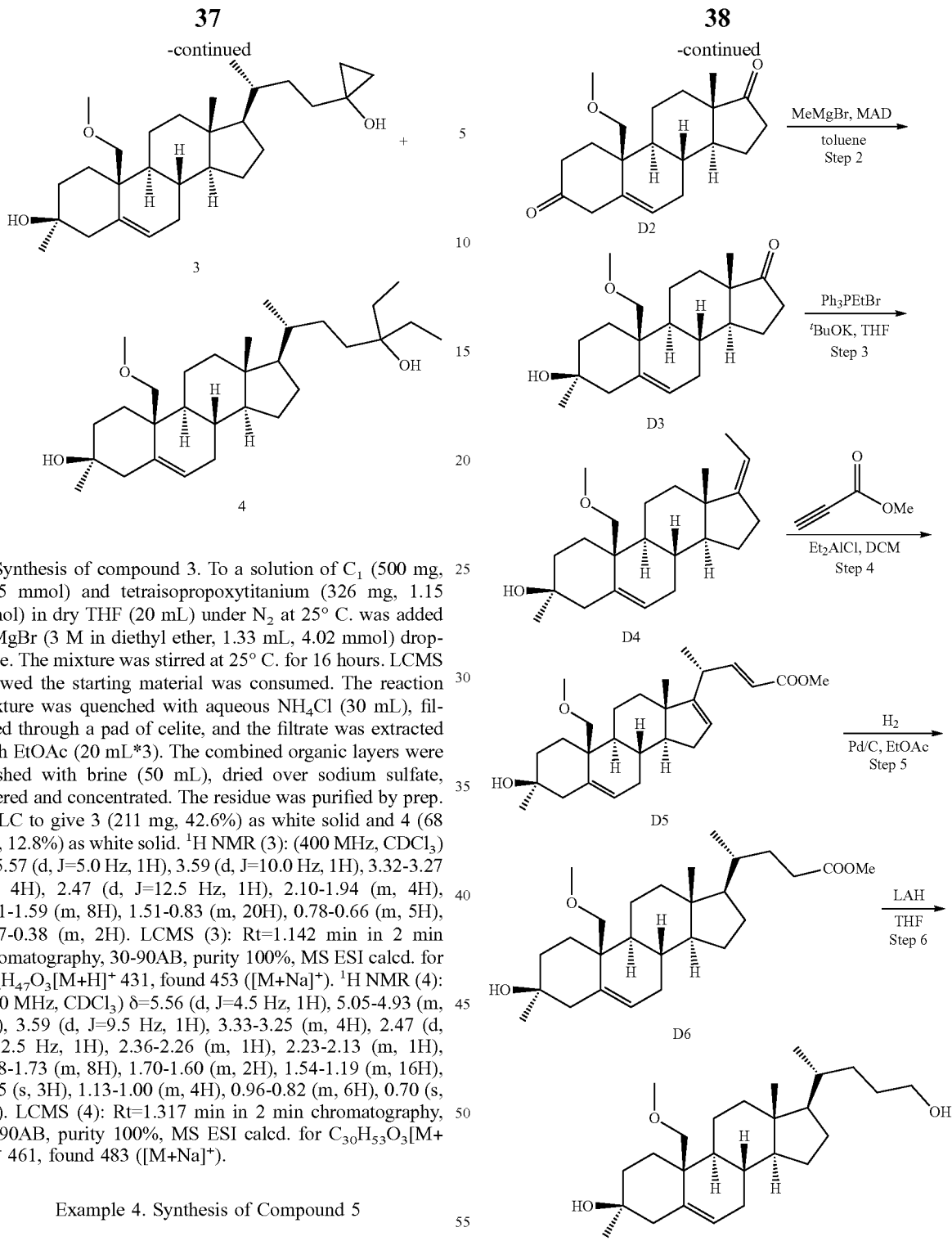

Synthesis of compound 3. To a solution of $C_1$ (500 mg, 1.15 mmol) and tetraisopropoxytitanium (326 mg, 1.15 mmol) in dry THF (20 mL) under $N_2$ at 25° C. was added EtMgBr (3 M in diethyl ether, 1.33 mL, 4.02 mmol) dropwise. The mixture was stirred at 25° C. for 16 hours. LCMS showed the starting material was consumed. The reaction mixture was quenched with aqueous $NH_4Cl$ (30 mL), filtered through a pad of celite, and the filtrate was extracted with EtOAc (20 mL*3). The combined organic layers were washed with brine (50 mL), dried over sodium sulfate, filtered and concentrated. The residue was purified by prep. HPLC to give 3 (211 mg, 42.6%) as white solid and 4 (68 mg, 12.8%) as white solid. $^1$H NMR (3): (400 MHz, $CDCl_3$) δ=5.57 (d, J=5.0 Hz, 1H), 3.59 (d, J=10.0 Hz, 1H), 3.32-3.27 (m, 4H), 2.47 (d, J=12.5 Hz, 1H), 2.10-1.94 (m, 4H), 1.91-1.59 (m, 8H), 1.51-0.83 (m, 20H), 0.78-0.66 (m, 5H), 0.47-0.38 (m, 2H). LCMS (3): Rt=1.142 min in 2 min chromatography, 30-90AB, purity 100%, MS ESI calcd. for $C_{28}H_{47}O_3[M+H]^+$ 431, found 453 ($[M+Na]^+$). $^1$H NMR (4): (400 MHz, $CDCl_3$) δ=5.56 (d, J=4.5 Hz, 1H), 5.05-4.93 (m, 1H), 3.59 (d, J=9.5 Hz, 1H), 3.33-3.25 (m, 4H), 2.47 (d, J=12.5 Hz, 1H), 2.36-2.26 (m, 1H), 2.23-2.13 (m, 1H), 2.08-1.73 (m, 8H), 1.70-1.60 (m, 2H), 1.54-1.19 (m, 16H), 1.15 (s, 3H), 1.13-1.00 (m, 4H), 0.96-0.82 (m, 6H), 0.70 (s, 3H). LCMS (4): Rt=1.317 min in 2 min chromatography, 30-90AB, purity 100%, MS ESI calcd. for $C_{30}H_{53}O_3[M+H]^+$ 461, found 483 ($[M+Na]^+$).

Example 4. Synthesis of Compound 5

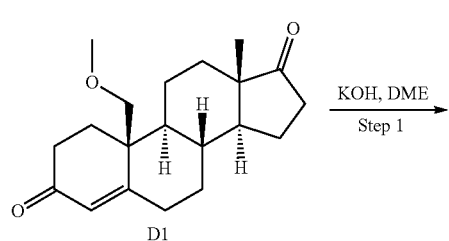

Synthesis of compound D2. To a solution of D1 (20 g, 63.2 mmol) in DME (200 mL) was added KOH (35.4 g, 0.632 mol). The mixture was stirred at 25° C. for 16 hours. TLC (PE:EA=2:1) showed the starting material was remained and the desired compound was observed. The reaction mixture was quenched with ice chips and aqueous citric acid (250 mL), extracted with EtOAc (200 mL*3). The combined organic layers were dried over anhydrous sodium sulfate, filtered and concentrated. The residue was purified by column chromatography on silica gel (PE:EA=5:1) to give D2 (3 g, 15.0%) as a white solid. $^1$H NMR (400 MHz, CDCl$_3$) δ=5.67-5.56 (m, 1H), 3.66 (d, J=10.0 Hz, 1H), 3.48 (d, J=10.0 Hz, 1H), 3.40-3.28 (m, 4H), 2.91 (dd, J=1.5, 16.6 Hz, 1H), 2.52-2.36 (m, 2H), 2.34-2.28 (m, 1H), 2.23-2.02 (m, 4H), 1.98-1.85 (m, 2H), 1.81-1.72 (m, 1H), 1.69-1.63 (m, 1H), 1.61-1.42 (m, 3H), 1.32-1.19 (m, 2H), 1.09-1.02 (m, 1H), 0.93 (s, 3H).

Synthesis of compound D3. To a stirred solution of D2 (24.8 g, 113 mmol) in toluene (100 mL) was added Me$_3$Al (2 M in toluene, 28.3 mL, 56.6 mmol) at 0° C. under N$_2$ dropwise. The resulting solution was stirred for 1 h at 25° C. It was cooled to −70° C. with dry-ice/acetone bath, and a slurry of (8R,9S,10S,13S,14S)-10-(methoxymethyl)-13-methyl-7,8,9,10,11,12,13, 14,15,16-decahydro-1H-cyclopenta[a]phenanthrene-3,17(2H,4H)-dione (6 g, 18.9 mmol) in toluene (150 mL) was added and then stirred for 1 h at −50 to −60° C. MeMgBr in diethyl ether (3M, 18.8 mL, 56.6 mmol) was then added dropwise, while maintaining the temperature during the addition between −50 to −40° C. The reaction mixture was then stirred for 3 h at −50 to −60° C. The mixture was quenched with 10% aqueous citric acid (200 mL), extracted with EtOAc (200 mL*3). The combined organic layers were washed with brine (400 mL), dried over anhydrous sodium sulfate, filtered and concentrated. The residue was purified by column chromatography on silica gel (PE:EA=8:1) to give D3 (4.5 g, 71.6%) as white solid. $^1$H NMR (400 MHz, CDCl$_3$) δ=5.61 (d, J=5.0 Hz, 1H), 3.65 (d, J=10.0 Hz, 1H), 3.33-3.26 (m, 4H), 2.54-2.39 (m, 2H), 2.17-2.02 (m, 4H), 1.98-1.81 (m, 3H), 1.72-1.61 (m, 3H), 1.57-1.47 (m, 3H), 1.29-1.17 (m, 2H), 1.16 (s, 3H), 1.12-1.04 (m, 1H), 0.99-0.88 (m, 4H). LCMS Rt=1.412 min in 7 min chromatography, 30-90AB, purity 100%, MS ESI calcd. for C$_{21}$H$_{33}$O$_3$[M+H]$^+$ 333, found 315 ([M+H−18]$^+$).

Synthesis of compound D4. To a solution of bromo(ethyl)triphenylphosphorane (18.3 g, 49.5 mmol) in THF (100 mL) under N$_2$ was added a solution of t-BuOK (5.55 g, 49.5 mmol) in THF (60 mL). The mixture was becoming orange and stirred for 1 hour. A solution of D3 (3.3 g, 9.92 mmol) in THF (40 mL) was added to this mixture, and the resultant mixture was stirred at 60° C. for additional 16 hours. The reaction mixture was quenched with aqueous NH$_4$Cl (200 mL), extracted with EtOAC (100 mL*2). The combined organic layers were washed with brine (200 mL), dried over anhydrous sodium sulfate, filtered and concentrated. The residue was purified by column chromatography on silica gel (PE:EA=10:1) to give D4 (2.5 g, 73.3%) as a white solid. $^1$H NMR (400 MHz, CDCl$_3$) δ=5.62-5.54 (m, 1H), 5.16-5.10 (m, 1H), 3.61 (d, J=10.0 Hz, 1H), 3.36-3.26 (m, 4H), 2.53-2.27 (m, 3H), 2.23-1.94 (m, 4H), 1.90-1.81 (m, 1H), 1.69-1.64 (m, 3H), 1.63-1.45 (m, 8H), 1.28-1.19 (m, 1H), 1.16 (s, 3H), 1.11-1.01 (m, 2H), 0.97-0.83 (m, 4H). LCMS Rt=1.506 min in 2 min chromatography, 10-80AB, purity 100%, MS ESI calcd. for C$_{23}$H$_{37}$O$_2$ [M+H]$^+$ 345, found 327 ([M+H−18]$^+$).

Synthesis of compound D5. To a solution of D4 (1.2 g, 3.48 mmol) and methyl propiolate (874 mg, 10.4 mmol) in dichloromethane (15 mL) under N$_2$ at 0° C. was added diethylaluminum chloride (0.9 M in toluene, 15.4 mL, 13.9 mmol) dropwise. The resultant mixture was stirred at 25° C. for 16 hours. TLC (PE:EA=3:1) showed the starting material was consumed. The reaction mixture was quenched with aqueous citric acid (100 mL) at 0° C. carefully. The mixture was extracted with dichloromethane (100 mL*3), and the combined organic layers were dried over anhydrous sodium sulfate, filtered and concentrated. The residue was purified with the other batch (SAGE-LGY-041) together by column chromatography on silica gel (PE:EA=10:1) to give D5 (3.5 g, 76.4%) as a white solid. $^1$H NMR (400 MHz, CDCl$_3$) δ=6.98-6.88 (m, 1H), 5.90-5.72 (m, 1H), 5.57 (d, J=4.0 Hz, 1H), 5.45-5.32 (m, 1H), 3.77-3.69 (m, 3H), 3.61 (d, J=10.0 Hz, 1H), 3.36-3.25 (m, 4H), 3.02 (t, J=6.4 Hz, 1H), 2.47 (d, J=12.4 Hz, 1H), 2.10-1.92 (m, 5H), 1.90-1.59 (m, 2H), 1.23-1.14 (m, 7H), 1.10-0.92 (m, 3H), 0.90-0.81 (m, 5H). LCMS Rt=1.176 min in 2 min chromatography, 30-90AB, purity 100%, MS ESI calcd. for C$_{27}$H$_{41}$O$_4$ [M+H]$^+$ 429, found 451 ([M+Na]$^+$).

Synthesis of compound D6. To a solution of D5 (2 g, 4.66 mmol) in EtOAc (50 mL) was added Pd/C (5% on carbon, 0.5 g). The mixture was degassed and purged with H$_2$ three times, and stirred at 25° C. under H$_2$ balloon for 2 hours. LCMS showed the starting material was consumed completely. The mixture was filtered through a pad of celite, and the filtrate was concentrated to give D6 (2 g, 99.5%) as a white solid. $^1$H NMR (400 MHz, CDCl$_3$) δ=5.56 (d, J=5.0 Hz, 1H), 3.66 (s, 3H), 3.59 (d, J=10.0 Hz, 1H), 3.32-3.26 (m, 4H), 2.46 (d, J=12.5 Hz, 1H), 2.40-2.30 (m, 1H), 2.26-2.17 (m, 1H), 2.08-1.92 (m, 4H), 1.89-1.73 (m, 3H), 1.68-1.59 (m, 2H), 1.54-1.23 (m, 7H), 1.15 (s, 3H), 1.13-0.99 (m, 4H), 0.95-0.83 (m, 5H), 0.70 (s, 3H). LCMS Rt=1.210 min in 2 min chromatography, 30-90AB, purity 100%, MS ESI calcd. for C$_{27}$H$_{45}$O$_4$[M+H]$^+$433, found 415 ([M+H−18]$^+$).

Synthesis of compound 5. To a solution of D6 (100 mg, 0.231 mmol) in dry THF (10 mL) at 0° C. was added LiAlH$_4$ (87.2 mg, 2.30 mmol) in portions carefully. The resultant slurry was stirred at 0° C. for 2 hours. TLC (PE:EA=3:1) showed the starting material was consumed. The reaction mixture was quenched with aqueous NH$_4$Cl (20 mL) at 0° C. dropwise carefully, filtered through a pad of celite, and the filtrate was extracted with EtOAc (10 mL*3). The combined organic layers were dried over anhydrous sodium sulfate and concentrated. The residue was purified by prep. HPLC to give 5 (32 mg, 34.2%) as a white solid. $^1$H NMR (400 MHz, CDCl$_3$) δ=5.56 (d, J=4.4 Hz, 1H), 3.65-3.56 (m, 3H), 3.34-3.25 (m, 4H), 2.47 (d, J=12.4 Hz, 1H), 2.08-1.94 (m, 4H), 1.87-1.73 (m, 2H), 1.68-1.56 (m, 4H), 1.50-1.21 (m, 9H), 1.17-1.00 (m, 8H), 0.97-0.84 (m, 5H), 0.71 (s, 3H). LCMS Rt=1.074 min in 2 min chromatography, 30-90AB, purity 100%, MS ESI calcd. for C$_{26}$H$_{45}$O$_3$[M+H]$^+$ 405, found 427 ([M+Na]$^+$).

Example 5. Synthesis of Compound 6

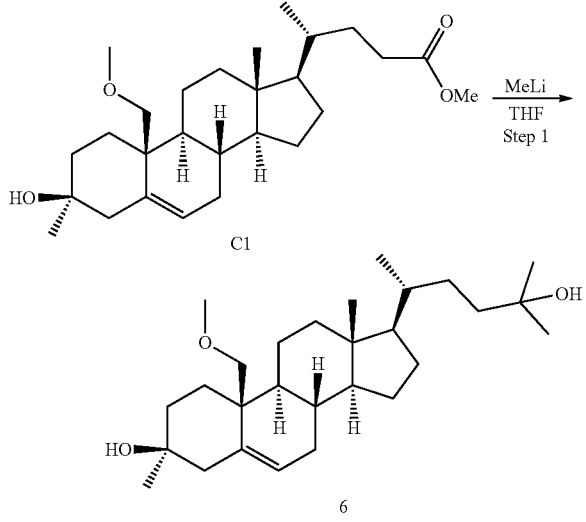

Synthesis of compound 6. To a solution of $C_1$ (100 mg, 0.231 mmol) in dry THF (10 mL) at 0° C. was added MeLi (1.6 M in diethyl ether, 0.72 mL, 25.2 1.15 mmol) dropwise. The mixture was stirred at 0° C. for 2 hours. TLC (PE:EA=3:1) showed the starting material was consumed. The reaction mixture was quenched with aqueous $NH_4Cl$ (20 mL) at 0° C., extracted with EtOAc (10 mL*3). The combined organic layers were dried over anhydrous sodium sulfate, filtered and concentrated. The residue was purified by prep. HPLC to give 6 (47 mg, 47.0%) as a white solid. $^1H$ NMR (400 MHz, $CDCl_3$)=5.56 (d, J=5.2 Hz, 1H), 3.59 (d, J=9.6 Hz, 1H), 3.34-3.26 (m, 4H), 2.47 (d, J=12.4 Hz, 1H), 2.08-1.94 (m, 4H), 1.87-1.74 (m, 2H), 1.68-1.55 (m, 4H), 1.51-1.25 (m, 9H), 1.19 (s, 6H), 1.17-1.00 (m, 8H), 0.96-0.84 (m, 5H), 0.70 (s, 3H). LCMS $t_R$=1.177 min in 2 min chromatography, 30-90AB, purity 100%, MS ESI calcd. for $C_{28}H^{49}O_3$ $[M+H]^+$ 433, found 455 ($[M+Na]^+$).

Example 6. Synthesis of Compound 7

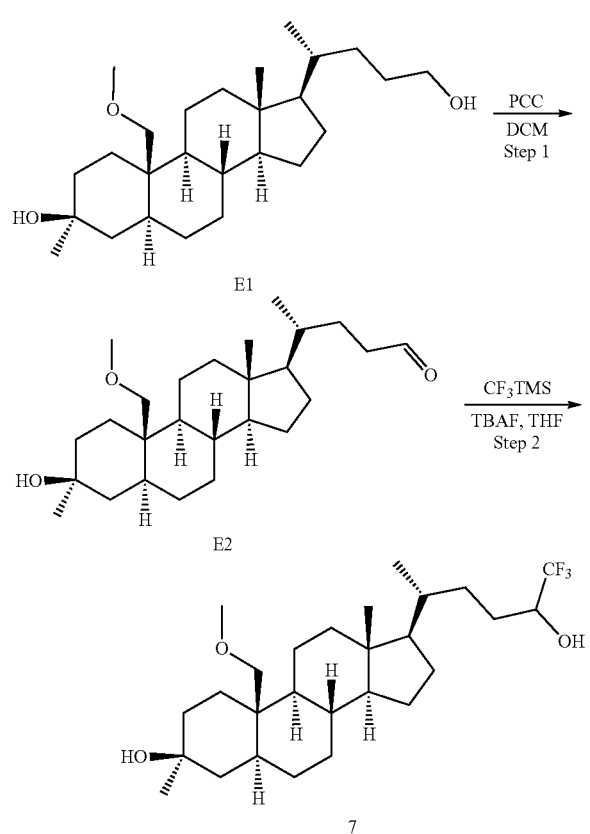

Synthesis of compound E2. To a solution of E1 (200 mg, 0.491 mmol) in DCM (10 mL) was added silica gel (200 mg) and PCC (212 mg, 0.982 mmol). The mixture was stirred at 25° C. for 16 hours. TLC (PE:EA=3:1) showed the starting material was consumed. The reaction mixture was filtered, and the filtrate was concentrated. The residue was purified by silica gel (PE:EA=10:1) to give E2 (100 mg, 50.5%) as colorless oil. LCMS Rt=1.201 min in 2 min chromatography, 30-90AB, purity 100%, MS ESI calcd. for $C_{26}H_{45}O_3$ $[M+H]^+$ 405, found 387 ($[M+H-18]^+$).

Synthesis of compound 7. To a solution of E2 (100 mg, 0.247 mmol) and trimethyl(trifluoromethyl)silane (174 mg, 1.23 mmol) in THF (5 mL) was added CsF (3.75 mg, 24.7 μmol). The mixture was stirred at 25° C. for 1 hour. TLC (PE:EA=3:1) showed the starting material was consumed. A solution of TBAF (1 M in THF, 1.23 mL, 1.23 mmol) was added to the mixture, and the resulting mixture was stirred at 25° C. for 16 hours. The reaction mixture was concentrated, and the residue was purified by column chromatography on silica gel (PE:EA=10:1) to give 7 (8 mg, 6.83%) as off white solid. $^1H$ NMR (400 MHz, $CDCl_3$) δ=3.92-3.79 (m, 1H), 3.52-3.43 (m, 2H), 3.30 (s, 3H), 2.21-1.91 (m, 4H), 1.89-1.60 (m, 7H), 1.52-1.40 (m, 3H), 1.39-1.18 (m, 9H), 1.16-0.97 (m, 5H), 0.97-0.75 (m, 5H), 0.73-0.62 (m, 4H). LCMS Rt=1.204 min in 2 min chromatography, 30-90AB, purity 100%, MS ESI calcd. for $C_{27}H_{46}F_3O_3$ $[M+H]^+$ 475, found 457 ($[M+H-18]^+$).

Example 7. Synthesis of Compound 8

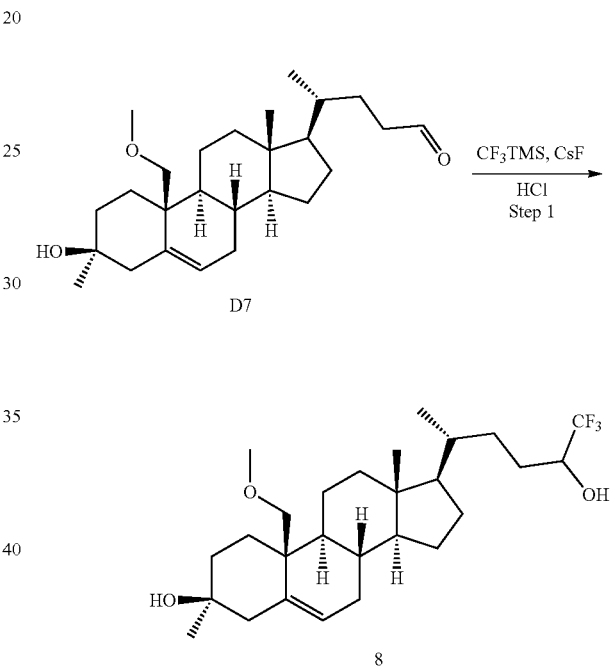

Synthesis of compound 8. To a solution of D7 (50 mg, 0.124 mmol) and trimethyl(trifluoromethyl)silane (88.1 mg, 0.62 mmol) in THF (2 mL) was added CsF (1.88 mg, 0.0124 mmol). The mixture was stirred at 25° C. for 1 hour. TLC (PE:EA=3:1) showed the starting material was consumed completely, and HCl (1 M in water, 1.24 mL, 1.24 mmol) was added to the reaction mixture. The resultant mixture was stirred at 25° C. for 16 hours. The desired compound was detected by TLC (PE:EA=3:1). The reaction mixture was neutralized with aqueous sodium bicarbonate (5 mL), extracted with EtOAc (5 mL*3), dried with anhydrous sodium sulfate, filtered and concentrated. The residue was purified by prep. HPLC to give 8 (5.5 mg, 9.38%) as white solid. $^1H$ NMR (400 MHz, $CDCl_3$) δ=5.57 (d, J=4.0 Hz, 1H), 3.94-3.78 (m, 1H), 3.60 (d, J=10.0 Hz, 1H), 3.39-3.23 (m, 4H), 2.47 (d, J=14.1 Hz, 1H), 2.10-1.92 (m, 5H), 1.89-1.69 (m, 4H), 1.46 (br. s., 4H), 1.38-1.04 (m, 12H), 1.03-0.80 (m, 6H), 0.71 (s, 3H). LCMS Rt=1.168 min in 2 min chromatography, 30-90AB, purity 100%, MS ESI calcd. for $C_{27}H_{44}F_3O_3$ $[M+H]^+$ 473, found 455 ($[M+H-18]^+$).

Example 8. Synthesis of Compound 9

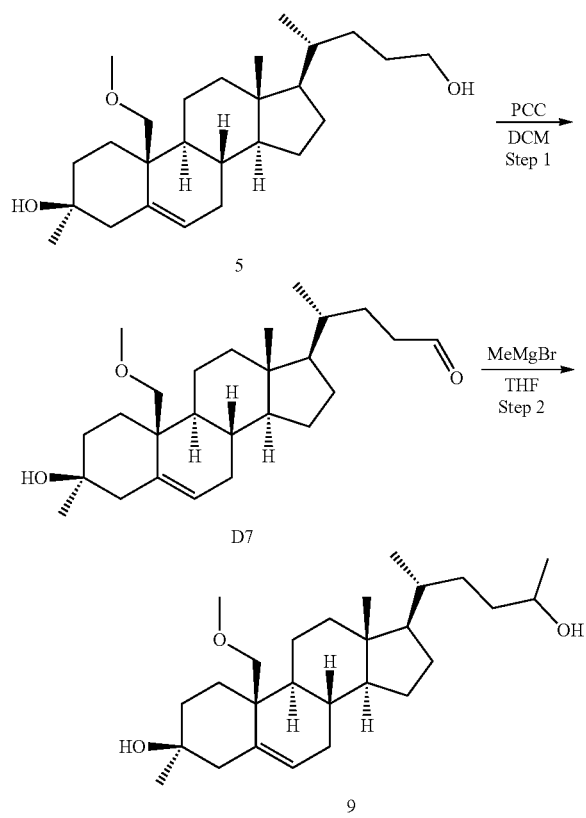

Synthesis of compound D7. To a solution of 5 (850 mg, 2.10 mmol) in DCM (15 mL) was added PCC (678 mg, 3.15 mmol) and silica gel (1 g). The mixture was stirred at 25° C. for 16 hours. TLC (PE:EA=3:1) showed the starting material was consumed. The reaction mixture was filtered, and the filtrate was concentrated. The residue was purified by column chromatography on silica gel (PE:EA=8:1) to give D7 (250 mg, 29.5%) as white solid. LCMS Rt=1.089 min in 2 min chromatography, 30-90AB, purity 45.2%, MS ESI calcd. for $C_{26}H_{43}O_3[M+H]^+$ 403, found 385 ($[M+H-18]^+$).

Synthesis of compound 9. To a solution of D7 (200 mg, 0.496 mmol) in dry THF (5 mL) at 0° C. was added MeMgBr (3 M in dimethyl ether, 0.83 mL, 2.48 mmol). The mixture was stirred at 25° C. for 2 hours. TLC (PE:EA=3:1) showed the starting material was consumed. The reaction mixture was quenched with saturated aqueous ammonium chloride (5 mL), extracted with EtOAc (5 mL*3), dried over sodium sulfate, filtered and concentrated to give 9 (190 mg, 91.7%) as white solid. One batch (140 mg) was used directly in the next step, and the other batch (50 mg) was purified by prep. HPLC to give desired compound (3 mg). $^1$H NMR (400 MHz, CDCl$_3$) δ=5.56 (d, J=5.0 Hz, 1H), 3.77-3.71 (m, 1H), 3.59 (d, J=10.0 Hz, 1H), 3.33-3.25 (m, 4H), 2.47 (d, J=13.1 Hz, 1H), 2.10-1.92 (m, 5H), 1.87-1.73 (m, 3H), 1.69-1.58 (m, 3H), 1.49-1.23 (m, 10H), 1.20-1.00 (m, 11H), 0.96-0.81 (m, 6H), 0.71 (s, 3H). LCMS R$_t$=1.126 min in 2 min chromatography, 30-90AB, purity 100%, MS ESI calcd. for $C_{27}H_{47}O_3$ $[M+H]^+$ 419, found 401 ($[M+H-18]^+$).

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm.

Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$·H$_2$O). Flow rate: 25 mL/min Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: XBridge C18, 4.6*50 mm, 3.5 μm at 45 C.

Assay Methods

Compounds of the present invention can be evaluated using various in vitro and in vivo assays described in the literature; examples of which are described below.

The following examples are offered to illustrate the biological activity of the compounds, pharmaceutical compositions, and methods provided herein and are not to be construed in any way as limiting the scope thereof.

NMDA Potentiation

NMDA potentiation was assessed using either whole cell patch clamp of mammalian cells which expressed NMDA receptors, or using two-electrode voltage clamp (TEVC) of *Xenopus laevis* oocytes expressing NMDA receptors.

Whole-Cell Patch Clamp of Mammalian Cells

The whole-cell patch-clamp technique was used to investigate the effects of compounds on the NMDA receptor (GRIN1/GRIN2A subunits) expressed in HEK cells. NMDA/Glycine peak and steady-state currents were recorded from stably transfected cells expressing the NMDA receptor and the modulatory effects of the test items on these currents were investigated. Results are shown on Table 1.

Cells were stably transfected with human GRIN1 (variant NR1-3). These cells were transiently transfected (Lipofectamine™) with GRIN2A cDNA and CD8 (pLeu) antigene cDNA. About 24-72 hours following transfection 1 μl Dynabeads M-45 CD8 was added to identify successfully transfected cells (Jurman et al., *Biotechniques* (1994) 17:876-881). Cells were passaged to a confluence of 50-80%. Cells were seeded onto Poly-L-Lysine coated cover slips covered with culture complete medium in a 35 mm culture dish. Confluent clusters of cells are electrically coupled (Pritchett et al., *Science* (1988), 242:1306-8). Because responses in distant cells are not adequately voltage clamped and because of uncertainties about the extent of coupling (Verdoorn et al., *Neuron* (1990), 4:919-28), cells were cultivated at a density that enables single cells (without visible connections to neighboring cells) to be measured. Cells were incubated at 37° C. in a humidified atmosphere with 5% $CO_2$ (rel. humidity about 95%). The cells were continuously maintained in and passaged in sterile culture flasks containing a 1:1 mixture of Dulbecco's modified eagle medium and nutrient mixture F-12 (D-MEM/F-12 1×, liquid, with L-Glutamine) supplemented with 9% fetal bovine serum and 0.9% Penicillin/Streptomycin solution. The complete medium was supplemented with 3.0 μg/ml Puromycin.

Whole cell currents were measured with HEKA EPC-10 amplifiers using PatchMaster software. Cell culture dishes for recordings were placed on the dish holder of the microscope and continuously perfused (1 ml/min) with "bath solution" (NaCl 137 mM, KCl 4 mM, $CaCl_2$) 1.8 mM, $MgCl_2$ 1 mM, HEPES 10 mM, D-Glucose 10 mM, pH (NaOH) 7.4). All solutions applied to cells including the pipette solution were maintained at room temperature (19° C.-30° C.). After formation of a Gigaohm seal between the patch electrodes and transfected individual HEK 293 cells (pipette resistance range: 2.5 MΩ-6.0 MΩ; seal resistance range: >1 GQ) the cell membrane across the pipette tip was ruptured to assure electrical access to the cell interior (whole-cell patch-configuration). At this point the bath solution is switched to "NMDA bath solution" (NaCl 137 mM, KCl 4 mM, $CaCl_2$) 2.8 mM, HEPES 10 mM, D-Glucose 10 mM, Cremophore 0.02%, pH (NaOH) 7.4). NMDA inward currents were measured upon application of 30 μM NMDA (and 5.0 μM Glycine) to patch-clamped cells (2 applications) for 5 s. The cells were voltage clamped at a holding potential of −80 mV. For the analysis of test articles, NMDA receptors were stimulated by 30 μM NMDA and 5.0 μM Glycine after sequential pre-incubation of increasing concentrations of the test article. Pre-incubation duration was 30 s. Stimulation duration was 5 s Test articles were dissolved in DMSO to form stock solutions of 0.1 mM and 1 mM. Test articles were diluted to 0.1 μM and 1 μM in "NMDA bath solution". Both concentrations of test articles were tested on each cell. The same concentration was applied at least three times or until the steady state current amplitude was reached. Every day one cell was tested with 50 μM PREGS (positive control) using the same application protocol to test whether cells were successfully transfected with NMDA receptors.

TABLE 1

| Structure | NMDA 1a2A (%) Potentiation 1 μM |
|---|---|
| (steroid structure) | A |
| (steroid structure) | A |
| (steroid structure) | A |
| (steroid structure) | B |
| (steroid structure) | C |

For Table 1, "A" indicates >5 to 50%; B: >50%; C indicates not active in the assay.

Whole-Cell Patch Clamp of Mammalian Cells (IWB)

The whole-cell patch-clamp technique was used to investigate the effects of compounds on NR1/NR2A glutamate receptors expressed in mammalian cells. The results are shown on Table 2.

Test article effects were evaluated in 8-point concentration-response format (4 replicate wells/concentration). All test and control solutions contained 0.3% DMSO and 0.01%

Kolliphor® EL ($C_{5135}$, Sigma). The test article formulations were loaded in a 384-well compound plate using an automated liquid handling system (SciClone ALH3000, Caliper LifeScienses). The measurements were performed using Ion Works Barracuda platform following this procedure: Electrophysiological Procedures:

a) Intracellular solution (mM): 50 mM CsCl, 90 mM CsF, 2 mM $MgCl_2$, 5 mM EGTA, 10 mM HEPES. Adjust to pH 7.2 with CsOH.

b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).

c) Holding potential: −70 mV, potential during agonist/PAM application: −40 mV.

Recording Procedure:

a) Extracellular buffer will be loaded into the PPC plate wells (11 μL per well). Cell suspension will be pipetted into the wells (9 μL per well) of the PPC planar electrode.

b) Whole-cell recording configuration will be established via patch perforation with membrane currents recorded by on-board patch clamp amplifiers.

c) Two recordings (scans) will be performed. First, during pre-application of PAM alone (duration of pre-application—5 min) and second, during test articles and agonist ($EC_{20}$ L-glutamate and 30 μM glycine) co-application to detect positive modulatory effects of the test article.

Test Article Administration: The first pre-application will consist of the addition of 20 μL of 2× concentrated test article solution and, second, of 20 μL of 1× concentrated test article and agonist at 10 μL/s (2 second total application time).

TABLE 2

| Structure | GluN2A PCA IWB Ephys % potentiation at 3 μM |
|---|---|
| 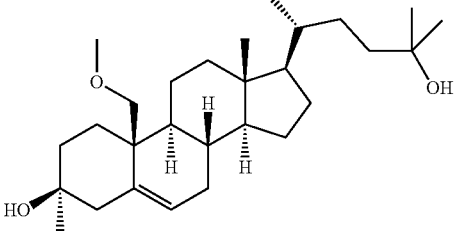 | A |
| 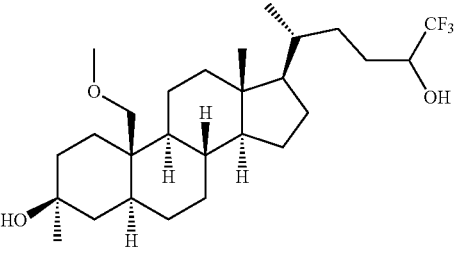 | B |

TABLE 2-continued

| Structure | GluN2A PCA IWB Ephys % potentiation at 3 μM |
|---|---|
| 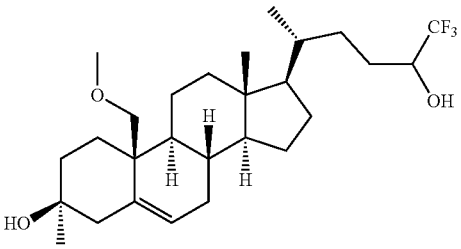 | A |
| 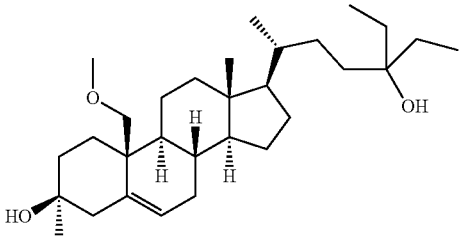 | A |
| 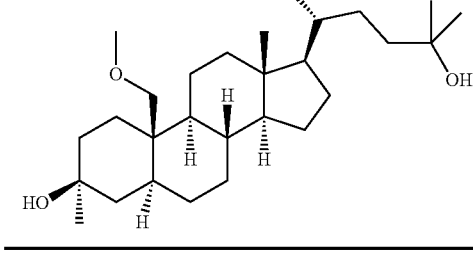 | A |

For Table 2, "A" indicates 10 to 150%, and "B" indicates potentiation of >150%.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

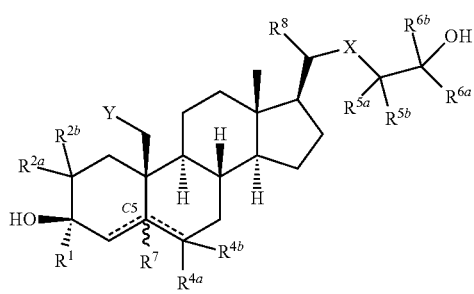

(I)

or a pharmaceutically acceptable salt thereof;
wherein:
$R^1$ is hydrogen, $C_1$-$C_6$ alkyl, $C_2$-$C_6$ alkenyl, $C_2$-$C_6$ alkynyl, carbocyclyl, or heterocyclyl;
each of $R^{2a}$ and $R^{2b}$ is independently hydrogen, $C_1$-$C_6$ alkyl, halo, cyano, —$OR^A$, or —$NR^BR^C$, or
$R^{2a}$ and $R^{2b}$ together with the carbon atom to which they are attached form a 3-7 membered ring;
each of $R^{4a}$ and $R^{4b}$ is independently absent, hydrogen, $C_1$-$C_6$ alkyl, or halo;

X is —$C(R^X)_2$— or —O—, wherein $R^X$ is independently hydrogen, halo, or one $R^X$ group and $R^{5b}$ are joined to form a double bond;
Y is —$OR^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, —$C(O)NR^BR^C$, or —$S(O)_2R^D$;
each instance of $R^{5a}$ and $R^{5b}$ is independently hydrogen, halo, or $C_1$-$C_6$ alkyl;
each of $R^{6a}$ and $R^{6b}$ is independently hydrogen, $C_1$-$C_6$ alkyl, $C_2$-$C_6$ alkenyl, $C_2$-$C_6$ alkynyl, carbocyclyl, heterocyclyl, aryl, or heteroaryl, or
$R^{6a}$ and $R^{6b}$, taken together with the carbon atom to which they are attached, form a 3-6 membered ring; or
$R^{5a}$ and $R^{6a}$, together with the carbon atoms to which they are attached, form a 3-6-membered ring; and
$R^7$ is absent or hydrogen in the alpha configuration;
$R^8$ is hydrogen, halo, $C_1$-$C_6$alkyl, carbocyclyl, or —$OR^A$;
═══ represents a single or double bond, wherein when one ═══ is a double bond, the other ═══ is a single bond;
wherein when the ═══ between —$CR^7$ and —$CR^{4a}R^{4b}$ is a double bond, then one of $R^{4a}$ or $R^{4b}$ is absent; and
when one of the ═══ is a double bond, $R^7$ is absent;
$R^A$ is hydrogen, $C_1$-$C_6$ alkyl, carbocyclyl, heterocyclyl, aryl, or heteroaryl;
each of $R^B$ and $R^C$ is independently hydrogen, $C_1$-$C_6$ alkyl, carbocyclyl, heterocyclyl, aryl, heteroaryl, or taken together with the atom to which they are attached form a 3-7-membered ring; and
$R^D$ is hydrogen, $C_1$-$C_6$ alkyl, carbocyclyl, heterocyclyl, aryl, or heteroaryl.

2. The compound of claim 1, or a pharmaceutically acceptable salt thereof, wherein $R^1$ is unsubstituted $C_{1\text{-}3}$ alkyl.

3. The compound of claim 1, or a pharmaceutically acceptable salt thereof, wherein $R^1$ is substituted $C_{1\text{-}3}$ alkyl.

4. The compound of claim 1, or a pharmaceutically acceptable salt thereof, wherein $R^{2a}$ or $R^{2a}$ is hydrogen.

5. The compound of claim 1, or a pharmaceutically acceptable salt thereof, wherein $R^{4a}$ is hydrogen.

6. The compound of claim 1, or a pharmaceutically acceptable salt thereof, wherein X is —$CH_2$—.

7. The compound of claim 1, or a pharmaceutically acceptable salt thereof, wherein $R^8$ is substituted or unsubstituted $C_{1\text{-}3}$ alkyl.

8. The compound of claim 1, wherein the compound of Formula (I) is a compound of Formula (II):

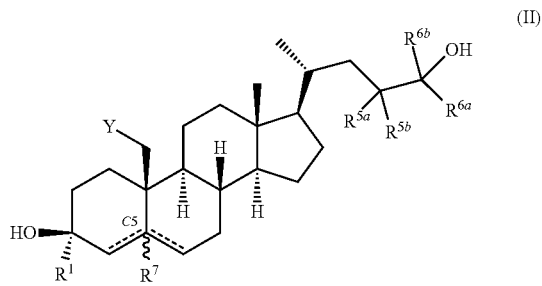

(II)

or a pharmaceutically acceptable salt thereof.

9. The compound of claim 8, wherein the compound of Formula (II) is a compound of Formula (II-A):

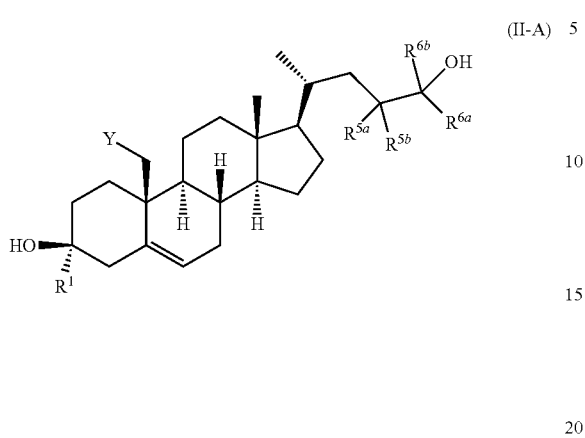

(II-A)

or a pharmaceutically acceptable salt thereof.

10. The compound of claim 8, wherein the compound of Formula (II) is a compound of Formula (II-B):

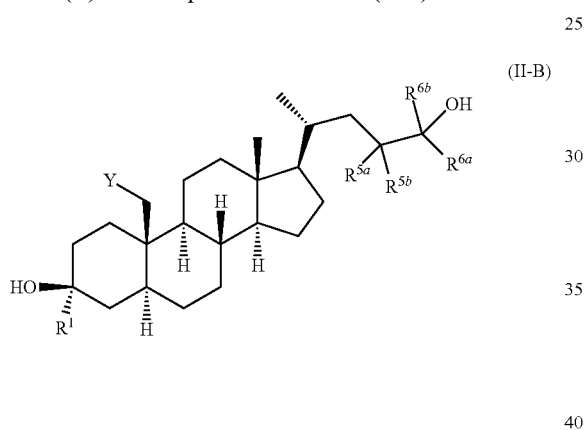

(II-B)

or a pharmaceutically acceptable salt thereof.

11. The compound of claim 1, or a pharmaceutically acceptable salt thereof, wherein $R^{5a}$ or $R^{5b}$ is hydrogen.

12. The compound of claim 1, or a pharmaceutically acceptable salt thereof, wherein $R^{6a}$ is a substituted or unsubstituted $C_{1-3}$ alkyl.

13. The compound of claim 1, or a pharmaceutically acceptable salt thereof, wherein $R^{6a}$ is a substituted or unsubstituted $C_{2-4}$ alkyl, substituted or unsubstituted $C^{2-3}$ alkenyl, substituted or unsubstituted $C^{2-3}$ alkynyl, or substituted or unsubstituted carbocyclyl.

14. The compound of claim 1, or a pharmaceutically acceptable salt thereof, wherein $R^{6b}$ is substituted or unsubstituted $C_{1-3}$ alkyl.

15. The compound of claim 1, or a pharmaceutically acceptable salt thereof, wherein $R^{6a}$ and $R^{6b}$, taken together with the atom to which they are attached, form a 3-6 membered ring.

16. The compound of claim 1, or a pharmaceutically acceptable salt thereof, wherein $R^Y$ is substituted or unsubstituted $C_{1-3}$ alkyl.

17. The compound of claim 1, or a pharmaceutically acceptable salt thereof, wherein $R^Y$ is substituted or unsubstituted heterocyclyl.

18. The compound of claim 1, wherein the compound is:

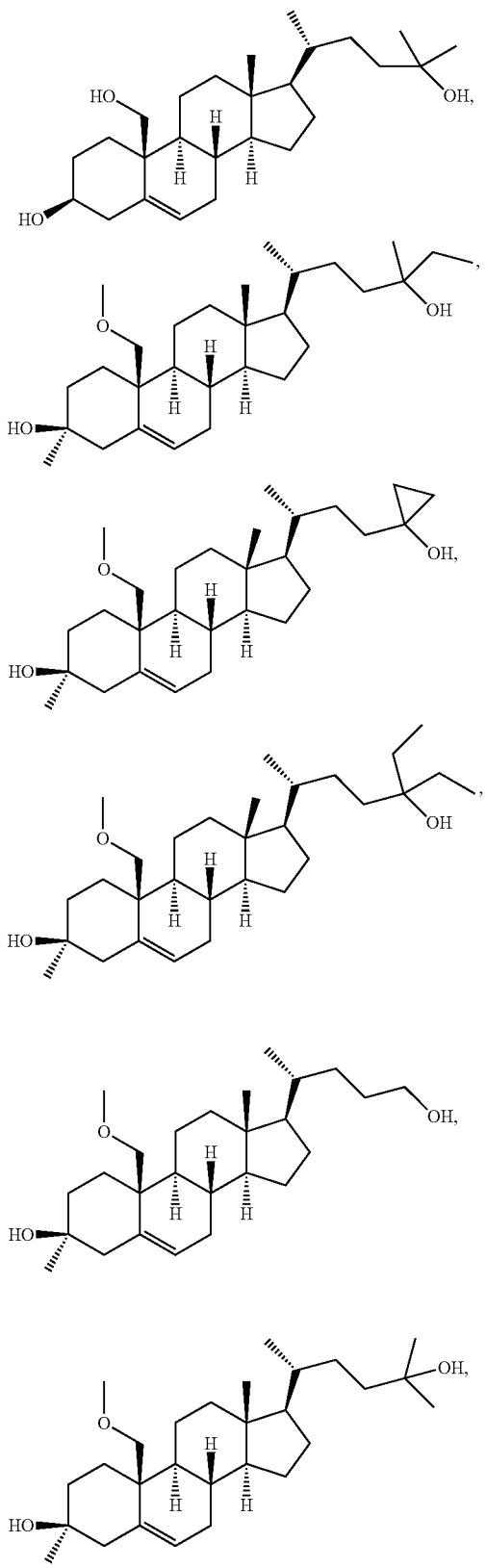

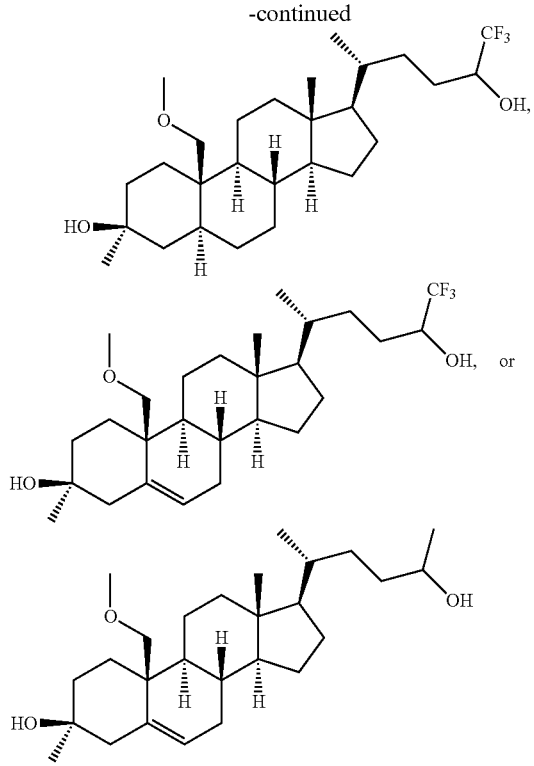
or a pharmaceutically acceptable salt thereof.
19. A pharmaceutical composition comprising the compound of claim 1, or a pharmaceutically acceptable salt thereof, and a pharmaceutically acceptable carrier.
20. The compound of claim 18, wherein the compound is:
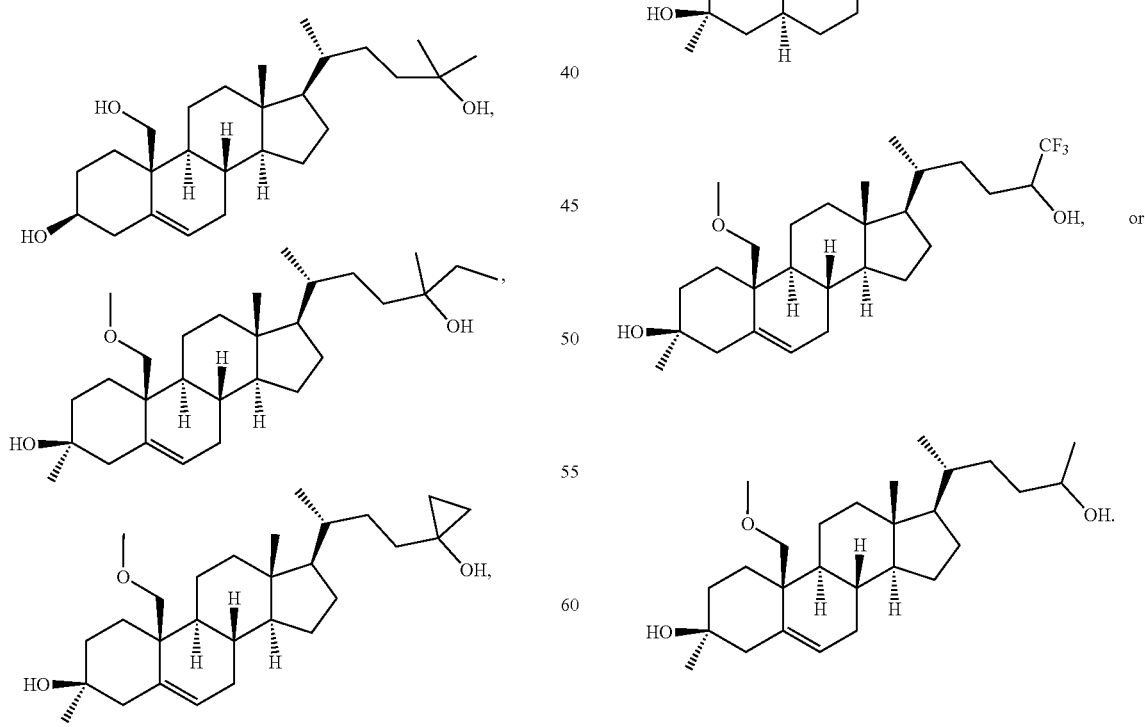
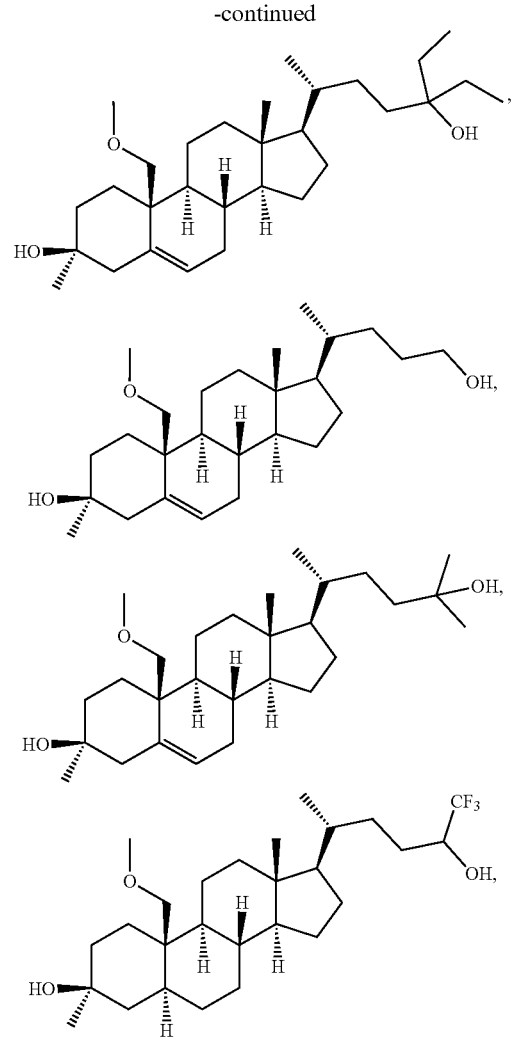
* * * * *